(12) United States Patent
Sudor

(10) Patent No.: US 6,709,692 B2
(45) Date of Patent: Mar. 23, 2004

(54) SURFACE ABSORBING POLYMERS AND THE USES THEREOF TO TREAT HYDROPHOBIC OR HYDROPHILIC SURFACES

(75) Inventor: Jan Sudor, Corbeil Essones (FR)

(73) Assignee: Genset S.A. (FR)

( * ) Notice: Subject to any disclaimer, the term of this patent is extended or adjusted under 35 U.S.C. 154(b) by 0 days.

(21) Appl. No.: 09/975,192

(22) Filed: Oct. 10, 2001

(65) Prior Publication Data

US 2002/0103352 A1 Aug. 1, 2002

Related U.S. Application Data

(60) Provisional application No. 60/326,091, filed on Sep. 28, 2001, and provisional application No. 60/239,316, filed on Oct. 10, 2000.

(51) Int. Cl.[7] .......................... A61L 31/08; A61L 33/00; B05D 1/00; B05D 3/00
(52) U.S. Cl. ...................... 427/2.1; 427/2.11; 427/2.13; 427/2.3; 427/155; 427/384
(58) Field of Search ................................ 427/2.1, 2.11, 427/2.13, 2.3, 155, 384

(56) References Cited

U.S. PATENT DOCUMENTS

| 4,783,441 A | * | 11/1988 | Thurow | 514/3 |
| 5,516,703 A | * | 5/1996 | Caldwell et al. | 436/532 |
| 5,962,136 A | * | 10/1999 | Dewez et al. | 428/410 |

FOREIGN PATENT DOCUMENTS

| EP | 1 016 584 A2 | 5/2000 | | |
| WO | WO 94/03544 | * | 2/1994 | C08L/101/00 |

OTHER PUBLICATIONS

Lee, J.H., et al.; "Surface properties of copolymers of alkyl methacrylates with methoxy (polyethylene oxide) methacrylates and their application as protein–resistant coatings"; Biomaterials 1990, vol. 11, Sep.; pp. 455–464; Butterworth–Heinemann Ltd.; 0142–9612/90/070455–10.

(List continued on next page.)

Primary Examiner—Shrive P. Beck
Assistant Examiner—Jennifer Kolb Michener
(74) Attorney, Agent, or Firm—Saliwanchik, Lloyd & Saliwanchik

(57) ABSTRACT

The invention provides methods for the treatment of surfaces using surface adsorbing polymers, methods for decreasing the adsorption of organic materials onto the surface of treated devices or vessels, methods for performing fluid operations involving the treatment of surfaces, and apparatus and systems comprising the treated surfaces. Further, the present invention provides a method for treating the surface of microfluidics channel wherein the microfluidics surface is coated for deactivation and wherein this coating can be easily regenerated. The present invention also provides a method for treating the surface of a plastic device. The surface adsorbing polymers of the invention are particularly stable at temperatures and conditions required for biochemical reactions, especially in applications involving temperature cycling or polymerization of polynucleotides or polypeptides.

41 Claims, 6 Drawing Sheets

OTHER PUBLICATIONS

Lee, J.H., et al.; "Protein–resistant surfaces prepared by PEO–containing block copolymer surfactants"; Journal of Biomedical Materials Research; vol. 23, pp. 351–368 (1989); John Wiley & Sons; 0021–9304/89/030351–18.

Amiji, M.,et al.; "Prevention of protein adsorptionand platelet adhesion on surfaces by PEO/PPO/PEO triblock copolymers"; Biomaterials, 1992, vol. 13, No. 10, pp. 682–692; Butterworth–Heinemann, Ltd.; 0142–9612/92/100682–11.

Shoffner, M.A. et al. "Chip PCR I. Surface Passication of Microfabricated Silicon–glass chips for PCR" Nucleic Acids Research, 1996, pp. 375–379, vol. 24, No. 2, Oxford University Press, Surrey, GB.

Giordano, Braden, et al. "Towards dynamic coating of glass microchip chambers for amplifying DNA via the polmerase chain reaction" Electrophoresis, 2001, pp. 334–340, vol. 22, No. 2.

Search Report for International Application No. PCT\US01\42631 (International Publication No. WO 02\030571A3).

* cited by examiner

C<C*        C=C*        C>C*

SURFACE ABSORBING POLYMERS AND THE USES THEREOF TO TREAT HYDROPHOBIC OR HYDROPHILIC SURFACES

RELATED APPLICATION INFORMATION

This application claims priority on U.S. provisional patent application Serial No. 60/239,316, filed Oct. 10, 2000, entitled "Methods for the Treatment and Regeneration of Microchannel Surfaces"; and, U.S. provisional patent application Serial No. 60/326,091, filed Sep. 28, 2001, entitled "Surface Adsorbing Polymers and the Uses Thereof to Treat Hydrophobic Surfaces".

FIELD OF THE INVENTION

This invention relates to methods for reducing the adsorption of organic materials (e.g., peptides, proteins, nucleic acids, and cells) onto hydrophobic or hydrophilic surfaces (e.g., polymeric surfaces). The invention also relates to devices, vessels and apparatus (e.g., microtiter plates, microfluidic channels and kits) having been treated by such methods and methods of performing fluid operations therein.

BACKGROUND

Biological materials such as peptides, proteins, nucleic acids, and cells are often stored, transferred or reacted in devices and apparatus such as multiwell plates, microcentrifuge tubes and pipettes made of plastic or other non-polar materials. It is a common observation that biological compounds adsorb/bind to the surfaces of such devices. This is also true for organic materials which exhibit some hydrophobicity in an aqueous solution, e.g., acridinium compounds, PCBs, etc.

For many applications, such binding is undesirable. For example, the binding results in the loss of valuable materials, such as, enzymes and antibodies, and can result in variations in the dispensing of organic materials, especially when small volumes are involved. The binding of proteins, cells, and platelets to hydrophobic surfaces is also of concern in a variety of blood handling procedures.

As a result of these considerations, extensive efforts have been made to provide methods for reducing the binding of proteins and other organic compounds to various surfaces. Examples of the approaches which have been considered can be found in Caldwell et al., U.S. Pat. No. 5,516,703; Ding et al., International Application Publication WO 94/03544; Amiji et al., Biomaterials, 13:682–692, 1992; J. Andrade, "Principles of Protein Adsorption" in Surface and Interfacial Aspects of Biomedical Polymers, J. Andrade, editor, Volume 2, Plenum Press, New York, 1–80, 1985; Lee et al., Polymeric Mater. Sci Eng., 57:613–617, 1987; Lee et al., Journal of Biomedical Materials Research, 23:351–368, 1989; Lee et al., Biomaterials, 11:455–464, 1990; Lee et al., Prog. Polym. Sci., 20:1043–1079, 1995; Merrill et al., ASAIO Journal, 6:60–64, 1983; Okano et al., Journal of Biomedical Materials Research, 20:1035–1047, 1986; Okkema et al., J. Biomater. Sci. Polymer Edn., 1:43–62, 1989; Owens et al., Journal of Cell Science, 87:667–675, 1987; Rabinow et al., J. Biomater. Sci. Polymer Edn., 6:91–109, 1994; Schroen et al., Journal of Membrane Science, 80:265–274, 1993; Sheu et al., J. Adhesion Sci. Technol., 6:995–1009, 1992; Shinada et al., Polymer Journal, 15:649–656, 1983; and Thurow et al., Diabetologia, 27:212–218, 1984.

Of particular interest is the treatment of small volume reaction devices that allow for multiple reactions under a variety of conditions. Such advances have been made in microfluidics and microtiter plate technology, therefore, there is a need for methods of treating these devices to decrease contamination, increase reaction yields and save valuable reagents.

Microfluidics involves using microchannels instead of test tubes or microplates to carry out analyses and reactions. These microchannels or microcircuits are etched into silicon, quartz, glass, ceramics or plastic. The size of these channels is of micrometer order, while the reaction volumes are of nanolitre or of microlitre order. The principle is to guide the reaction media, which contain reagents and samples, over zones which correspond to the different steps of the protocol. The integration of reactors, chromatographic columns, capillary electrophoresis systems and miniature detection systems into these microfluidic systems allows the automation of complex protocols by integrating them into one single platform. These "laboratories on chips" have made it possible to obtain results which are efficient in terms of reaction speed, in terms of product economy and in terms of miniaturization which allows the development of portable devices. Remarkable results have also been obtained for the integration and automation of complex protocols, such as biochemical or molecular biology protocols which often require numerous manipulations. These manipulations comprise in particular mixing reagents and samples, controlling the reaction temperature, carrying out thermal cycling and detection. Wolley et al. (Anal. Chem., 68, 4081–4086, 1996), for example, described the integration of a PCR microreactor, a capillary electrophoresis system and a detector in a single device. A device on a chip which allows the integration of a step for mixing the reagents and an enzymatic reaction has been described by Hadd et al. (Anal. Chem., 69, 3407–3412, 1997). This device provides a microcircuit of channels and reservoirs etched into a glass substrate, and moving and mixing of the fluids takes place by electrokinetics. Numerous microfluidic systems for the integration of protocols and of analyses have thus been described in particular in international patent application WO 98/45481, the disclosure of which is incorporated herein by reference.

One of the great difficulties in implementing these devices resides in the high adsorption of samples and reagents to the channel surface during the movement of the fluids through the channel. In general, microfluidic devices contain channels in a micrometer size-range that have large surface-to-volume ratios (~10–100 times greater than a surface-to-volume ratio in conventional microtiter plates). This leads to an increased significance of the surface properties/quality/chemistry in microfluidic devices. At the same time, biological samples (e.g., protein samples, or reaction mixtures such as PCR mix, LCR mix, microsequencing (MIS) mix, etc.) are complex mixtures of large and small molecules of different polarities (e.g., DNA and protein molecules, dNTPs, ddNTPs, fluorescent labels, etc.) that may have a strong affinity to solid substrates, as well as for liquid/liquid and liquid/air interfaces. Proteins in particular are known to adsorb strongly to silica materials (Righetti, P. G., ed., 1996, *Capillary Electrophoresis in Analytical Biotechnology*, CRC series in Analytical Biotechnology, CRC Press, Boca Raton). For these reasons, surfaces in microfluidic devices are deactivated prior performing biological reactions in such microstructures. Deactivation of a surface reduces adsorption of organic materials onto the surface. Without deactivation of surfaces, biological reactions generally cannot be performed in silicon (silica) microchannels [Shoffner, M. A. et al., Nucleic Acids Res. 24: 375–379 (1996) and Cheng, J. et al., Nucleic Acids Res. 24: 380–385 (1996)].

Several possibilities for surface deactivation have been shown. Generally, the deactivation strategy depends on the material from which a microfluidic device is made. For example, silica surfaces (silicon chips) can be chemically functionalized, e.g., through silanisation reactions (Snyder, L. R., Kirkland, J. J., Introduction to modern chromatography, Wiley-Interscience, 1979, New York; Shoffner, M. A. et al., Nucleic Acids Res 24: 375–379 (1996); and Kopp, M. et al., Science, 280: 1046–1048 (1998)). The silanized chips can directly be used for biological reactions or may further be modified by preparation of a polymer coating layer on the surface.

Surface deactivation using coatings involves two approaches: covalent and non-covalent coatings. The stability of covalent coatings, some of which are referred to as polymer brushes, and adsorbed polymer layers depends on three factors: (a) the chemical stability of the surface, (b) the stability of the polymer-surface interaction, and (c) the chemical stability of the polymer that is used for a surface modification. Generally, with respect to the stability of a single polymer/surface interaction (a), a covalent bond (covalent coatings) is more stable than a non-covalent polymer/surface interaction (a fraction of a $k_B T$ unit, where $k_B$ is the Boltzman constant and T is temperature) in adsorbed polymer layers. However, due to a large number of segments (sometimes more than 10% of the total number of segments/monomers in a polymer) interacting with a surface in adsorbed polymer layers, the total adsorption energy per a single polymer molecule can be very large, reaching several $k_B T$ units and thus rendering the polymer adsorption virtually irreversible.

Covalent coatings have involved either growth of a polymer chain from a functionalized silica surface [Hjerten, S., J. Chromatogr., 347, 191–198 (1985); and Cobb, K. A. et al., Anal. Chem., 62: 2478–2483 (1990)] and/or grafting of a polymer chain onto a silica surface [Herren, B. J. et al., J. Colloid Interface Sci., 115:46 (1987); and Balachander, N. et al., Langmuir 6: 1621 (1990), Burns, N. L. et al., Langmuir 11:2768 (1995)]. The surface deactivation through chemical reactions involves formation of covalent linkages between functional groups on a surface (—OH) and a reactive silane or a functionalized polymer molecule [e.g., a silanized polyethylene glycol (PEG)]. This chemical modification of surfaces, often carried out in organic solvents, is time consuming and requires several synthetic steps before completion. Thus, this strategy of surface deactivation is generally expensive and not well adapted to modify large quantities of chips in a simple manner. The covalent chemical linkages (especially "—Si—O—X" bonds) are prone to a hydrolysis (e.g., at an alkaline pH) degrading the covalent coatings over time [Cobb, K. A. et al., Anal. Chem., 62, 2478–2483 (1990)]. Since these coatings cannot be simply regenerated, the life-time of such surfaces and consequently the whole devices is finite, and day-to-day reproducibility of the quality of a surface in chemically modified microfluidic devices is poor. Moreover, a good batch-to-batch reproducibility is hard to maintain due to, e.g., surface impurities and/or control of the humidity of the organic solvents used.

Another possibility for deactivating a microfluidics surface with a non-covalent coating is the adsorption of bovine serum albumin (BSA) onto a surface. BSA has been successfully employed for surface deactivations in PCR chips [Northrup, M. A., Anal. Chem., 70: 918–922 (1998); Waters, L. C. et al., Anal. Chem., 70: 158–162 (1998); and Waters, L. C. et al., Anal. Chem., 70:5172–5176 (1998)]. BSA adsorbs onto silica, saturates surface adsorption sites and enables to perform biological reactions in devices with high surface-to-volume ratios. However, BSA denatures at temperatures above 55–65° C. and, consequently, may coagulate and form large aggregates (depending on the BSA concentration) [Wetzel, R. et al., Eur. J. Biochem. 104: 469–478 (1980); and Oakes, J., J. Chem. Soc. Faraday, I72: 228–237 (1976)]. This coagulation (denaturation) of BSA at a high temperature is irreversible, i.e., the BSA does not re-dissolve in aqueous solutions when the temperature is decreased. When biological reactions are performed in a static mode (no liquid flow), e.g., in micro-wells, the surface deactivation by BSA is robust and works well [Northrup, M. A., Anal. Chem. 70: 918–922 (1998), Waters, L. C., Anal. Chem., 70: 158–162 (1998); and Waters, L. C., Anal. Chem., 70: 5172–5176 (1998)]. However, when biological reactions are carried out in a flow (i.e., there is a non-zero shear stress at the solid/liquid interface) and in small channels, large BSA aggregates in a solution may be transported downstream and, eventually, block a microchannel or a capillary. Thus, the disadvantage of using BSA for surface deactivations in microfluidic devices where reagents are transported from one place to the other by a liquid flow is the BSA's solubility change in a temperature range commonly used for biological reactions (PCR, LCR, MIS, etc.).

Although the use of polymers to prevent the adsorption of samples and reagents to microfluidic surfaces has been discussed thus far, the same techniques may be applied to other surfaces, such as surfaces made of silicon, quartz, glass, ceramics or plastic (polymeric), and other interfaces (i.e., liquid/liquid and liquid/air interfaces). These surfaces may include, but are not limited to, the surfaces of apparatus used for storing, dispensing, or reacting fluid samples, such as test tubes, multi-well plates, pipettes, pipette tips, microtiter plates, reaction wells or microcentrifuge tubes.

Such treatment techniques have a particular application to microtiter plates because they are used for biological reactions, often requiring successive steps in the same reaction well at small volumes. For example, genotyping process by single base extension method requires three successive biological reactions (i.e., polymerase chain reaction (PCR), enzymatic purification and microsequencing (MIS)). Thus it is efficient and beneficial to perform two or more successive reactions in the same well of one unique microtiter plate. In such cases, it must be assured that there is no inter-reaction contamination, and that biomolecules from previous reactions do not contaminate subsequent reactions. However this can prove difficult to achieve due to the high adsorption of residual biomolecules onto the surface of the microtiter plate, or high concentration of such molecules into liquid/liquid or liquid/air interfaces.

Many apparati, such as microtiter plates are non-polar, while biomolecules (e.g., protein samples, or reaction mixtures such as PCR reagents and MIS reagents) are complex mixtures of large and small molecules of different polarities (e.g., DNA and protein molecules, dNTPs, ddNTPs, fluorescent labels, etc.) that often have strong affinities to solid substrates. Adsorption of biomolecules onto the surface of the microtiter plate renders these biomolecules non-accessible or less accessible to enzymes during biological reactions.

One commonly encountered problem is adsorption of deoxynucleotides (dNTPs) onto the surface of microtiter plates, particularly during genotyping processes. Adsorption of dNTPs added during the first step of a genotyping procedure (i.e., PCR) onto the surface of a microtiter plate render them less accessible to shrimp alkaline phosphatase (SAP) during subsequent steps (i.e., enzymatic purification), and the adsorbed dNTPs are not dephosphorylated. As dNTPs release from the surface of the microtiter plate at high temperature (e.g., during the denaturation of EXO and SAP enzymes or during the temperature cycling of the MIS reactions), they can dramatically contaminate the third step of the genotyping process (i.e., MIS). As a result, the MIS oligonucleotide product may be extended by more than one base (dNTPs); thus the SNP specific fluorenscently-labeled ddNTPs may be incorrectly incorporated into the oligonucleotide product several bases downstream from the SNP site of interest. Consequently, this can lead to errors in genotyping (e.g., a homozygous sample can appear as a heterozygous one) when a detection technique without size-discrimination capability is employed. However, an additional prolongation of a MIS oligonucleotide by dNTPs left from a PCR causes a decrease of a specific signal that may be disadvantageous for any detection technique employed.

Another disadvantage related to adsorption of biomolecules onto the surface of a microtiter plate is a reduced yield of biological reactions. Absorption of valuable biomolecules results in decreased yields of the desired product. In an attempt to offset the loss of reagents to absorption, reagent concentrations are often increased to saturate the absorption sites on the plate surfaces. However, this is not an economical solution for preventing absorption.

A possibility for preventing contamination is to transfer the samples into a new microtiter plate between the two successive reactions. In the case of a genotyping process, PCR is performed in one microtiter plate and enzymatic purification followed by MIS is performed in another microtiter plate. However, this method of preventing contamination is not completely effective as about 10% of MIS reactions are still contaminated by leftover dNTPs from PCR reactions (data from Genset, Analyse Genomique Department). This contamination becomes more evident when reactions are performed in very small volumes (e.g., high-density plates), as the number of interactions of molecules from bulk solution with surfaces increases rapidly when the reaction volume decreases. Furthermore, it is technically more convenient and cheaper to use a method that does not require the transfer of samples to a new microtiter plate.

There is therefore a need for a method of deactivating surfaces which provides good day-to-day reproducibility of the quality of a surface in the same chip, microtiter plate or other surface, provides a stable surface at the relevant temperatures for biological applications, and does not involve complicated and expensive synthesis processes.

SUMMARY OF THE INVENTION

The invention provides for methods of using polymers for competitive adsorption to a surface to decrease the adsorption of organic materials (e.g., biomolecules) in fluid (e.g., aqueous) samples onto said surfaces. Alternatively, the invention provides for methods of using polymers to decrease the adsorption of organic materials onto liquid/air or liquid/liquid interfaces. Said surfaces may be made of silicon, quartz, glass, ceramics or plastic such as, e.g., polystyrene, polypropylene, polymethyl methacrylate, polyvinyl chloride, polyethylene, polycarbonate, polysulfone, fluoropolymers, polyamides, polydimethylsiloxanes, polyurethane, polysulfone, polytetrafluoroethylene, and elastomers. These surfaces may include, but are not limited to, the surfaces of apparati such as devices or vessels used for storing, dispensing, or reacting fluid samples. Such apparati comprise, but are not limited to, test tubes, multi-well plates, pipettes, pipette tips, microtiter plates, reaction wells, microchannels, microfluidic apparati, capillaries and microcentrifuge tubes. The invention further includes methods for performing fluid operations on said surfaces such that the adsorption of organic materials in a fluid sample is minimized by the introduction of surface adsorbing polymers. Fluid operations include, but are not limited to, reactions, incubations, dilutions, titrations, purifications, detections, mixing, binding assays, drug screening assays, and measuring assays (e.g., measurement of kinetics). Also preferred are fluid operations involving an enzyme. Fluid samples include, but are not limited to, reaction mixtures, such as PCR mixtures, LCR mixtures, primer extension reaction mixtures and genotyping reaction mixtures (e.g., microsequencing mixture). Preferred fluid samples are aqueous fluid samples. Organic materials include biomolecules, such as nucleic acids (e.g., DNA, RNA, polynucleotides, oligonucleotides, nucleotides, dNTPs such as dATP, dTTP, dCTP, dGTP, and ddNTPs such as ddATP, ddTTP, ddCTP, ddGTP), amino acids (e.g., proteins polypeptides, peptides, amino acids such as asparatate, glutamate, lysine, arginine, histidine, alanine, valine, leucine, isoleucine, phenylalanine, methionine, tryptophane, proline, serine, threonine, asparagine, glutamine, glycine, cysteine, and tyrosine) lipids, chemical compounds (e.g., fluorescent labels), and more specifically receptors or antibodies and their ligands, cells and growth factors, growth inhibitors, enzymes and substrates. Preferably, biomolecules may comprise complex mixtures of large and small molecules of different polarities such as the molecules listed above that may have a strong affinity to various surfaces. Any genius or species of surfaces, apparati, fluid operations or organic materials listed above may be specifically included or excluded from the embodiments of the invention.

The methods of the invention also relate to embodiments allowing the dynamic regeneration of surfaces where fluid samples are run sequentially in an apparatus such as a device or vessel (e.g., microchannel). Further, the methods of the invention relate to embodiments allowing for subsequent fluid operations to be performed sequentially on the same surface such that contamination is minimized and reaction yields are maximized.

Introducing surface adsorbing polymers that bind non-covalently to a surface prevents the undesired adsorption of organic materials onto the surface, thus reducing contamination and increasing reaction yields. Preferably, the surface is of smaller polarity than the polarity of an aqueous fluid sample. Such non-covalent coatings have several important advantages over chemical (covalent) coatings used in fluid operations: non-covalent deactivation methods do not involve complicated and time consuming chemical synthesis and are therefore inexpensive and well adapted to modify in a simple manner large quantities of apparatus for storing, dispensing or reacting fluid samples.

In a first aspect, the invention encompasses a method of decreasing adsorption of an organic material onto a surface, comprising: a) adding a fluid sample comprising said organic material and a surface adsorbing polymer to said surface, wherein said surface adsorbing polymer is capable of binding non-covalently to said surface. In a preferred embodiment, the surface is made of silicon, quartz, glass, ceramics or plastic (e.g., polystyrene, polypropylene, polymethyl methacrylate, polyvinyl chloride, polyethylene, polycarbonate, polysulfone, fluoropolymers, polyamides, polydimethylsiloxanes, polyurethane, polysulfone, polytetrafluoroethylene, and elastomers). Further, the organic material is a complex mixture of large and small molecules of different polarities such as the biomolecules listed above, which may have a strong affinity to the surface of the apparatus. A fluid sample may comprise a reaction mixture, such as a PCR reaction mixture, a LCR mixture, a primer extension reaction mixture or a genotyping reaction mixture (e.g., microsequencing (MIS) mixture). In another preferred embodiment, the surface adsorbing polymer is from a family of polyacrylamides, such as polyacrylamide (PAM), N-isopropylacrylamide (NIPAM) and polydimethylacrylamide (PDMA). In other preferred embodiments, other polymers, such as propylene glycol (PG) and ethylene glycol (EG), and polyglycols including polypropylene glycols (PPG) and polyethylene glycols (PEG) may be used as surface adsorbing polymers. In still other preferred embodiments, other polymers, such as propylene oxide (PO) and ethylene oxide (EO), and polyoxides including polypropylene oxides (PPO) and polyethylene oxides (PEO) may be used as surface adsorbing polymers. In further preferred embodiments, the surface adsorbing polymer is polydimethylsiloxane (PDMS) or polyvinylpyrolidone. In most preferred embodiments, block copolymers of the polymers listed herein are used, including for example block copolymers of PPG and PEG and PAM and NIPAM and PDMS. Any genus or species of surface adsorbing polymer may be specifically included or excluded from the embodiments of the invention. BSA is specifically excluded from the surface adsorbing polymers of the present invention.

In another aspect, the invention encompasses a method of decreasing adsorption of an organic material onto a surface, comprising: (a) obtaining a fluid sample comprising an organic material; (b) adding an effective amount of a surface adsorbing polymer to said fluid sample (c) contacting said fluid sample comprising said organic material and said surface adsorbing polymer to a surface; and (d) performing one or more fluid operations. Preferred fluid samples do not normally comprise any surface adsorbing polymer of the present invention prior to performing fluid operation. Alternatively, the fluid samples may normally comprise a surface adsorbing polymer of the present invention prior to performing one of the methods of the invention. Preferred fluid operations are fluid operations that do not normally involve any surface adsorbing polymer of the present invention. Other preferred fluid operations are reactions wherein said surface adsorbing polymer is not one of the reactants or wherein said surface adsorbing polymer has no activating or inhibiting effect on the reactants. Still other preferred fluid operations are reactions wherein said surface adsorbing polymer is not necessary for the reaction to occur. Alternatively, the surface adsorbing polymer may be one of the reactants of the fluid operation. Alternatively, the surface adsorbing polymer is added in excess, either in mass or molarity, compared to what is needed or normally used for performing a fluid operation. Preferably, the surface adsorbing polymer is in at least 2, 3, 4, 5, 6, 7, 8, 9, 10, 20, 50, 100, 500, 1000, 5000, or 10,000 fold excess to what is needed to perform the reaction where the surface adsorbing polymer is a reactant or to the amount normally used where the surface adsorbing polymer is not a reactant. In a preferred embodiment, said surface is part of an apparatus that is used for storing, dispensing, or reacting fluid samples, and may include, but is not limited to, a microchannel, a test tube, a multi-well plate, a pipette, a pipette tip, a microtiter plate, a reaction well, a microchannel or a microcentrifuge tube.

In still another aspect, the invention encompasses a method of decreasing adsorption of an organic material onto the surface of an apparatus, comprising: (a) providing an apparatus comprising or consisting essentially of a surface; (b) adding a fluid sample comprising said organic material and a surface adsorbing polymer to said apparatus, wherein said surface adsorbing polymer is capable of binding non-covalently to said surface; and (c) performing one or more fluid operations in same said apparatus.

In another aspect, the invention encompasses a method of selecting the quantity of a surface adsorbing polymer that is added to a fluid operation, comprising the steps of: (a) providing an apparatus comprising consisting essentially of a surface; (b) adding a fluid sample comprising an organic material and a surface adsorbing polymer to said apparatus, wherein said surface adsorbing polymer is capable of binding non covalently to said surface; (c) performing one or more fluid operations in same said apparatus; and (d) selecting the optimum quantity of said surface adsorbing polymer capable of obtaining the highest yield. Preferably, said surface of smaller polarity than the polarity of said fluid sample. Preferably, said fluid operation is PCR.

In another aspect, the invention encompasses a method of selecting the quantity of a surface adsorbing polymer that is added to a fluid operation, comprising the steps of: (a) providing an apparatus comprising or consisting essentially of a surface; (b) adding a fluid sample comprising an organic material and a surface adsorbing polymer to said apparatus, wherein said surface adsorbing polymer is capable of binding non covalently to said surface; (c) performing one or more fluid operations in same said apparatus; and (d) selecting the optimum quantity of said surface adsorbing polymer to decrease adsorption or contamination the greatest. Optionally, said contamination of subsequent fluid operations results from the presence of undesired dNTPs due to adsorption to a surface. Preferably, said surface is of smaller polarity than the polarity of said fluid sample. Preferably, said fluid operation is microsequencing and said contamination or adsorption is detectable by the presence of sequencing artifacts.

In another aspect, the invention encompasses a kit, comprising: (a) a fluid sample for performing a fluid operation; (b) a surface adsorbing polymer in an aqueous solution; and (c) a notice recommending the quantity of said surface adsorbing polymer that should be added to the fluid sample. Optionally, said kit comprises also an apparatus consisting essentially of a surface. Optionally, said surface absorbing polymer is comprised in a reaction mixture. Preferably, the recommended quantity of said surface adsorbing polymer that should be added to the fluid sample is selected using one of the methods of the present invention. Preferably, said kit is a genotyping kit.

In still another aspect, the invention encompasses a reaction mixture for performing fluid operations, wherein said reaction mixture comprises a surface adsorbing polymer of the present invention, and wherein the quantity of said surface adsorbing polymer that is comprised in said reaction mixture was selected using the methods of the present invention. Preferably, the reaction mixture is a PCR reaction mixture, a LCR mixture, a primer extension reaction mixture or a genotyping reaction mixture (e.g., microsequencing (MIS) mixture).

In preferred embodiments, the invention encompasses a method of dynamically maintaining or regenerating the polymer coating adsorbed on the surface of a microchannel comprising: (a) providing a channel disposed in a substrate; (b) introducing to said channel at least two fluid sample zones, wherein each of said at least two fluid sample zones comprises a fluid sample of interest; and (c) providing at least one separating fluid zone located between two of said fluid sample zones, wherein said at least one separating fluid zone or at least one fluid sample zone comprises a surface adsorbing polymer capable of binding non-covalently to a surface of said channel. Optionally, at least one fluid sample zone comprises a surface adsorbing polymer. Optionally, at least one separating fluid zone comprises a surface adsorbing polymer. Optionally, at least two fluid sample zones are substantially free of said surface adsorbing polymer. Optionally, at least one fluid separating zone and at least one fluid sample zone comprises a surface adsorbing polymer. Optionally, each of said fluid sample zones comprises a surface adsorbing polymer. Optionally, each fluid separating zone comprises a surface adsorbing polymer. Optionally, each fluid separating zone and each fluid sample zone comprises a surface adsorbing polymer. Optionally, at least any one integer between 1 and 100 fluid sample zones are provided in a channel, wherein each integer may be specifically included or excluded from embodiments of the present invention. Optionally, at least one fluid sample zone and said at least one separating fluid zone are flowing in the channel.

In other aspects, the invention encompasses a method of treating the surface of a microchannel comprising: (a) providing a channel disposed in a substrate; (b) introducing to said channel a first fluid zone, wherein said first fluid zone comprises a surface adsorbing polymer capable of binding non-covalently to a surface of said channel; and (c) introducing sequentially to said channel a second fluid zone comprising a fluid sample of interest, wherein said second fluid zone is substantially free of said surface adsorbing polymer when introduced to said channel. The surface refers to the interface between the microchannel and the fluid zone. In preferred embodiments, the surface adsorbing polymer is from a family of polyacrylamides, such as polyacrylamide (PAM), N-isopropylacrylamide (NIPAM) and polydimethylacrylamide (PDMA). In other preferred embodiments, other polymers, such as propylene glycol (PG) and ethylene glycol (EG), and polyglycols including polypropylene glycols (PPG) and polyethylene glycols (PEG) may be used as surface adsorbing polymers. In still other preferred embodiments, other polymers, such as propylene oxide (PO) and ethylene oxide (EO), and polyoxides including polypropylene oxides (PPO) and polyethylene oxides (PEO) may be used as surface adsorbing polymers. In further preferred embodiments, the surface adsorbing polymer is polydimethylsiloxane (PDMS) or polyvinylpyrolidone. In most preferred embodiments, block copolymers of the polymers listed herein are used, including for example block copolymers of PPG and PEG and PAM and NIPAM and PDMS, and further including block copolymers such as polyacrylamide-block-N-isopropylacrylamide (PAM-NIPAM) and polydimethylsiloxane-block-polyethyleneglycol (PDMS-PEG).

In yet further aspects, the invention encompasses a method of dynamically maintaining or regenerating the polymer coating adsorbed on the surface of a microchannel comprising: (a) providing a channel disposed in a substrate; and (b) introducing to said channel at least two fluid sample zones, wherein each of said at least two fluid sample zones comprises a fluid sample of interest, and wherein each of said at least two fluid sample zones comprises a surface adsorbing polymer capable of binding non-covalently to a surface of said channel.

In preferred embodiments of the invention, at least 2 fluid zones or fluid sample zones are provided in an individual channel. In particularly preferred embodiments, at least any one integer between 5 and 1000 fluid zones or fluid sample zones are provided in an individual channel. Preferably, adjacent fluid zones or fluid sample zones are separated by at least one fluid separating zone.

Where fluid samples and the surface adsorbing polymer are to be provided in the presence of one another, fluid samples and polymer solutions may be introduced to an apparatus of the invention either as a mixture or separately; separately introduced samples and polymers may be mixed in the apparatus.

In preferred embodiments, the polymer solution flows through the channel. Preferably, as described further, the polymer solution is moved through the channel in a continuous flow. In further preferred methods, movement of a fluid such as a solution, fluid sample zone or fluid separating zone in a channel is effected by pressure gradient. Optionally, movement of said solution is effected by an electroosmotic, electrokinetic, electro-hydrodynamic or by a temperature gradient system.

In further aspects, the invention relates to a method of performing a fluid operation in an apparatus comprising: (a) introducing a solution comprising a surface adsorbing polymer to the apparatus such that the polymer non-covalently adsorbs onto the apparatus surface; (b) introducing a fluid sample to said apparatus; and (c) performing a fluid operation in said apparatus. Preferably, said apparatus is a microtiter plate or a microfluidic apparatus.

The invention also encompasses microchannels and microfluidics devices comprising channels treated according to the methods of the invention. Specifically, the invention relates to a channel or a microfluidics device comprising a substrate and at least one channel disposed in said substrate, wherein the channel has non-covalently adsorbed thereon a surface adsorbing polymer according to the invention. Preferably, the channel has a width of between about 1 $\mu$m and about 3 mm. Preferably, said substrate consists essentially of silicon, quartz, glass, ceramics or plastic such as, e.g., polystyrene, polypropylene, polymethyl methacrylate, polyvinyl chloride, polyethylene, polycarbonate, polysulfone, fluoropolymers, polyamides, polydimethylsiloxanes, polyurethane, polysulfone, polytetrafluoroethylene, and elastomers.

Microfluidics devices of the invention may further comprise means for creating a pressure gradient across said channel, thereby effecting the movement of fluid in said channel, and/or a temperature regulation means for control of the temperature of the fluid in said channel.

The methods of the invention further comprise performing at least one fluid operation in said channel and/or said device. The methods of the invention are particularly suited to performing sequential fluid operations. The methods of the invention may comprise performing at least any one integer between 2 and 1000 fluid operations in a channel or apparatus.

In another aspect, the invention encompasses the use of a surface adsorbing polymer in a fluid sample for performing a fluid operation in a apparatus, wherein said surface adsorbing polymer is selected from the group consisting of the family of polyacrylamides, such as polyacrylamide (PAM), N-isopropylacrylamide (NIPAM) and polydimethylacrylamide (PDMA). In other preferred embodiments, other polymers, such as propylene glycol (PG) and ethylene glycol (EG), and polyglycols including polypropylene glycols (PPG) and polyethylene glycols (PEG) may be used as surface adsorbing polymers. In still other preferred embodiments, other polymers, such as propylene oxide (PO) and ethylene oxide (EO), and polyoxides including polypropylene oxides (PPO) and polyethylene oxides (PEO) may be used as surface adsorbing polymers. In further preferred embodiments, the surface adsorbing polymer is polydimethylsiloxane (PDMS) or polyvinylpyrolidone. In most preferred embodiments, block copolymers of the polymers listed herein are used, including for example block copolymers of PPG and PEG and PAM and NIPAM and PDMS, and further including block copolymers such as polyacrylamide-block-N-isopropylacrylamide (PAM-NIPAM) and polydimethylsiloxane-block-polyethyleneglycol (PDMS-PEG). Optionally, said step of performing a fluid operation comprises performing a fluid operation selected from the group consisting of a reaction, incubation, dilution, titration, purification, detection and drug screening assay, binding assays, and measuring assays (e.g., measurement of kinetics).

In further preferred embodiments of the methods, systems and apparatus of the invention, a fluid sample or fluid sample of interest comprise a test analyte or reagent. More preferably, a fluid sample comprises an organic material. Preferably, said organic material is a biomolecule, wherein said biomolecule can be selected from the group consisting of: nucleic acids (e.g., DNA, RNA, polynucleotides, oligonucleotides, nucleotides, dNTPs such as dATP, dTTP, dCTP, dGTP, and ddNTPs such as ddATP, ddTTP, ddCTP, ddGTP), amino acids (e.g., polypeptides, peptides, amino acids such as asparatate, glutamate, lysine, arginine, histidine, alanine, valine, leucine, isoleucine, phenylalanine, methionine, tryptophane, proline, serine, threonine, asparagine, glutamine, glycine, cysteine, and tyrosine), lipids, chemical compounds, and more specifically receptors or antibodies and their ligands, cells and growth factors and growth inhibitors, and enzymes and substrates. Said biomolecule may comprise complex mixtures of large and small molecules of different polarities (e.g., nucleic acids and protein molecules, dNTPs, ddNTPs, fluorescent labels, etc.) that may have a strong affinity to solid substrates. Any number of biomolecules may be included or excluded as individual species of the invention. In other aspects, a fluid sample may comprise a reaction mixture, such as a PCR reaction mixture, a LCR mixture, a primer extension reaction mixture or a genotyping reaction mixture (e.g., microsequencing (MIS) mixture), any of which may be included or excluded as species of the invention.

The methods, systems and apparatus of the invention can be used advantageously in accordance with a wide range of fluid operations, some of which are described further herein. In some aspects, the step of performing a fluid operation can comprise performing a fluid operation selected from the group consisting of a reaction, incubation, dilution, titration, purification, detection, mixing and drug screening assay, any of which may be included or excluded as species of the invention. In preferred embodiments of the invention, the fluid operation comprises performing a biochemical reaction. More specifically, a biochemical reaction may comprise primer extension reaction, temperature cycling, nucleic acid amplification reaction, or enzyme purification, any of which may be included or excluded as species of the invention. Particularly preferred temperature cycling reactions include PCR or MIS reactions. Any number or combination of fluid operations may be performed according to the methods of the invention. In one aspect, a apparatus is used for a single fluid operation, which in other aspects, at least 2 sequential fluid operations are performed in a channel or apparatus of the invention. Preferably, said sequential fluid operations are performed in the same channel or apparatus of the invention. In a preferred embodiment, the invention is directed to fluid operations in volumes of less than any integer between 20 and 0.1 $\mu$l. Any integer may be specifically included or excluded from the embodiments of the present invention.

Preferred surfaces which make up apparatus of the invention are made of or consist essentially of glass, quartz, silicon, metals or plastics, any of which may be included or excluded as species of the invention. Preferably said plastic is a polymeric, and, further preferred, said polymeric is a polymer of various polarities. The surface may be polar, non-polar, hydrophilic or hydrophobic. Preferred surfaces are polar hydrophobic surfaces, non-polar hydrophobic surfaces, polar hydrophilic surfaces, and non-polar hydrophilic surfaces, any of which may be included or excluded as species of the invention. Still further preferred, the polymer is selected from the group consisting of polystyrene, polypropylene, polymethyl methacrylate, polyvinyl chloride, polyethylene, polycarbonate, polysulfone, fluoropolymers, polyamides, polydimethylsiloxanes, polyurethane, polysulfone, polytetrafluoroethylene, and elastomers, any of which may be included or excluded as species of the invention. As used herein, the term substrate refers to a structural surface beneath a covering or coating (e.g., polymer coating). In the present invention, microchannels may be disposed in a substrate or apparati may be made of a substrate. In a preferred embodiment, the term apparatus is used interchangeably herein with device or vessel. Apparatus of the invention are used for storing, dispensing or reacting fluid samples. Said apparatus comprise both devices and vessels such as channels disposed in a substrate, or test tubes, multi-well plates, pipettes, pipette tips, microtiter plates, reaction wells, microchannels, microfluidic apparati, capillaries and microcentrifuge tubes test tubes, multi-well plates, pipette tips, microtiter plates, reaction wells, microcentrifuge tubes, microchannels, and the like comprising said surface, any of which may be included or excluded as species of the invention. Preferably said channel is a microchannel. Microchannels of the invention, including the microchannels disposed in the microfluidic devices of the invention, preferably have a width of between about 1 $\mu$m and about 3 mm.

In certain aspects, the surface of said devices, vessels or apparatus is an untreated surface; preferably an unsilanized surface when using a silicon substrate. Said surface may be hydrophobic or hydrophilic. In other aspects, the surface may be pretreated prior to treatment with a polymer according to the invention.

The invention also relates to microfluidic devices comprising reaction wells, and to fluid operations performed in a reaction well. In one embodiment, the invention comprises moving a fluid sample through or performing a fluid operation in a channel treated according to the methods of the invention, and performing a biochemical reaction in a reaction well treated according to the methods of invention. Preferably, said reaction well is in a microtiter plate. More preferably, said microtiter plate are polypropylene microtiter plates. Microtiter plates of the invention preferably are high density microtiter plates, such as microtiter plates having 96, 384, 1536 or more wells.

In particularly preferred embodiments of the invention, the surface adsorbing polymer is a water soluble polymer or a non-polar liquid soluble polymer; in other preferred embodiments the surface adsorbing polymer is an uncharged polymer. Preferably, the polymer is a silica-adsorbing polymer. In further preferred embodiments, the polymer has a molecular weight of at least $1\times10^3$, $5\times10^3$, $1\times10^4$, $5\times10^4$, $1\times10^5$, $5\times10^5$, $1\times10^6$ or $5\times10^6$ daltons. Most preferably, the polymer has a molecular weight of at least $1\times10^6$ daltons. Preferably, the surface adsorbing polymer is selected from the family of polyacrylamides. Further preferred, said surface adsorbing polymer is selected from the family of polyacrylamides, such as polyacrylamide (PAM), N-isopropylacrylamide (NIPAM) and polydimethylacrylamide (PDMA). In other preferred embodiments, other polymers, such as propylene glycol (PG) and ethylene glycol (EG), and polyglycols including polypropylene glycols (PPG) and polyethylene glycols (PEG) may be used as surface adsorbing polymers. In still other preferred embodiments, other polymers, such as propylene oxide (PO) and ethylene oxide (EO), and polyoxides including polypropylene oxides (PPO) and polyethylene oxides (PEO) may be used as surface adsorbing polymers. In further preferred embodiments, the surface adsorbing polymer is polydimethylsiloxane (PDMS) or polyvinylpyrolidone. In most preferred embodiments, block copolymers of the polymers listed herein are used, including for example block copolymers of PPG and PEG and PAM and NIPAM and PDMS, and further including block copolymers such as polyacrylamide-block-N-isopropylacrylamide (PAM-NIPAM) and polydimethylsiloxane-block-polyethyleneglycol (PDMS-PEG), any of which may be included or excluded as species of the invention. The polymer may be in aqueous or non aqueous solution. In a most preferred embodiment, the surface adsorbing polymer has a greater affinity for the surface than the biomolecules of the fluid sample. Most preferably, the total adsorption energy per a single polymer molecule reaches at least one or more $k_BT$ units.

In addition to the methods and apparatus of the invention, the invention also encompasses compositions comprising the surface adsorbing polymers of the invention. Included, for example, as further described herein, are compositions comprising a surface adsorbing polymer according to the invention and a fluid sample of interest, wherein the surface adsorbing polymer is not one of the reactants. These compositions may, for example, be prepared and subsequently provided as a mixture to an apparatus of the invention.

The invention further comprises uses of a surface adsorbing polymer, in particular for performing a fluid operation in a microchannel or a plastic apparatus, wherein the surface adsorbing polymer is not one of the reagents of the fluid operation, or wherein said surface adsorbing polymer has no activating or inhibiting effect on the reactants, or wherein said surface adsorbing polymer is not necessary for the reaction to occur. The surface adsorbing polymer can be used as an additive in a mixture comprising a sample, e.g. on which a fluid operation is to be performed. Preferably, said fluid operation is an operation selected from the group consisting of a mixing step, a reaction, an incubation, a dilution, a titration, a detection, a drug screening assay, a binding assay, and a measuring assay (e.g., measurement of kinetics). Most preferably, the fluid operation is a biochemical reaction; more preferably, the biochemical reaction involves temperature cycling.

DETAILED DESCRIPTION

Figure 1:
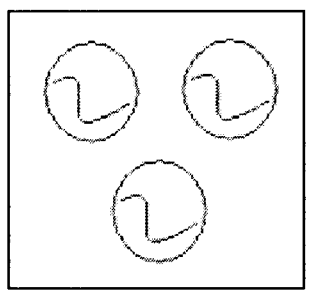
FIG. 1 shows a representation of the interaction of polymer chains in two different regimes, with the cross-over between them, as a function of polymer concentration.
Figure 1:
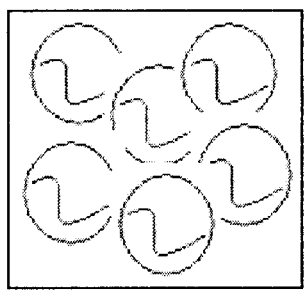
Figure 1:
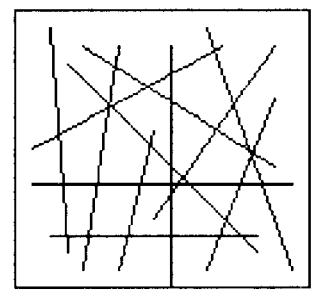

Fluid operations, particularly biological reactions, often require successive steps in the same apparatus at small volumes in order to maximize efficiency and minimize cost. For example, genotyping by single base extension requires three successive biological reactions [i.e., polymerase chain reaction (PCR), enzymatic purification and microsequencing (MIS)]. Thus it is efficient and beneficial to perform two or more successive reactions in the same apparatus. In such cases, it must be assured that there is no inter-reaction contamination due to adsorption, and that biomolecules from previous reactions do not contaminate subsequent reactions due to unwanted adsorption. However, this can prove difficult to achieve due to the high adsorption of residual biomolecules onto the surfaces of apparati.

Therefore, the invention provides methods for decreasing the adsorption of organic materials onto various surfaces using surface adsorbing polymers. Specifically, methods for performing fluid operations involving the addition of surface adsorbing polymers that bind non-covalently to a surface, thus preventing the undesirable adsorption of organic molecules onto said surface. The invention also provides apparatus and systems (e.g., kits) comprising surface adsorbing polymers. Further, the present invention provides a method for treating the surface of microfluidics channel wherein the microfluidics surface is coated for deactivation and wherein this coating can be easily regenerated. The surface adsorbing polymers of the invention are stable at temperatures and conditions required for biochemical reactions, especially in applications involving temperature cycling or polymerization of polynucleotides or polypeptides.

The surface deactivation method of the invention also provides a means for the dynamic coating of a surface with a surface adsorbing polymer. Preferably, the surface has not been pretreated in order to reduce adsorption of organic materials onto the surface. The dynamic coating method allows a surface to be regenerated as often as needed, increasing the life span of a apparatus which comprises the surface, and increasing the batch-to-batch reproducibility of any surface of the invention. This method also avoids the need for a special pretreatment of the surface.

As used herein, the term substrate refers to a structural surface beneath a covering or coating (e.g., polymer coating). A substrate may be silicon, quartz, glass, ceramics or plastic (e.g., polystyrene, polypropylene, polymethyl methacrylate, polyvinyl chloride, polyethylene, polycarbonate, polysulfone, fluoropolymers, polyamides, polydimethylsiloxanes, polyurethane, polysulfone, polytetrafluoroethylene, and elastomers.). Preferably, a plastic substrate comprises polystyrene. In the present invention, microchannels may be disposed in a substrate or devices may be made of a substrate. Preferably, the substrate is a plastic of smaller polarity than the polarity of an aqueous fluid sample.

As used herein, the term apparatus includes the terms device and vessel is used interchangeably with apparatus throughout the application. An apparatus refers to any element, tool, or component designed for a specific use or purpose. Said uses include storing, dispensing or reacting samples, preferably fluid samples. Examples of apparatus include, but are not limited to, microchannels, microfluidic apparati, capillaries, test tubes, multi-well plates, pipettes, pipette tips, microtiter plates, reaction wells and microcentrifuge tubes.

As used herein, the term microtiter plate refers to a multiwell plate used for storing and/or reacting fluid samples or performing fluid operations. Typically the plates are made of substrates such as silicon, quartz, glass, ceramics or plastic, and contain 96, 384, 1536, or more wells. The same microtiter plates may be used to perform successive fluid operations. Preferably, said fluid operations are biochemical reactions, such as temperature cycling (e.g., PCR), enzyme purification, primer extension reaction (e.g., MIS).

As used herein, the term channel encompasses the term microchannel. Also, as used herein, a microfluidics substrate refers to a solid substrate in which a microchannel is disposed. A microfluidics device comprises a microfluidics substrate, which typically comprises more than one microchannel, and optionally comprises other components or features related to performing a fluid operation such as reservoirs, inlet/outlet ports, as well as detection apparatus, reagent storage and distribution means, temperature regulation means, etc.

Based on the novel deactivation method, the invention also provides methods of conducting fluid operations, particularly chemical and biochemical reactions, and particularly fluid operations comprising the manipulations of fluids containing biomolecules.

A fluid operation as used herein refers to any fluid manipulation involving the movement of fluids or performing a task in a liquid phase. Fluid operations include but are not limited to reactions, incubations, separations, dilutions, titrations, mixing, purifications, detections, drug screening assays, binding assays, measuring assays (e.g., measurement of kinetics)as well as any operation generally involving a large number of successive manipulations, and any fluid manipulation where the fluid comprises a test analyte, reagent or biomolecule, particularly when the test analyte or reagent is a biomolecule.

As used herein, a chemical reaction or biochemical reaction refers to a process in which one or more substances are changed chemically or biochemically into one or more different substances (for example: reactant+reactant(s)– optionally any catalyst(s)→product(s). A biochemical reaction is typically a reaction mediated by or involving a biomolecule.

A reaction mixture refers to a single mixture containing the components necessary for a chemical or biochemical reaction to take place. Examples include, but are not limited to, PCR mixture and MIS mixture.

As used herein, a fluid sample or fluid sample of interest encompasses but is not limited to any molecule on which a fluid operation is to be performed, encompassing any biomolecule or chemical molecule. A fluid sample or fluid sample of interest includes but is not limited to a test analyte or a reagent. The term test analyte encompasses a substance being measured in an analytical procedure, which may include chemicals as well as biomolecules. A reagent refers to a reactant in a chemical or biochemical reaction.

As used herein, a biomolecule refers to an organic molecule that is synthesized by a living organism, and derivatives, variants and fragments thereof. Preferred biomolecules are macromolecules. Further preferred biomolecules comprise, but are not limited to, nucleic acids (e.g., DNA, RNA, polynucleotides, oligonucleotides, nucleotides, dNTPs such as dATP, dTTP, dCTP, dGTP, and ddNTPs such as ddATP, ddTTP, ddCTP, ddGTP), amino acids (e.g., proteins polypeptides, peptides, amino acids such as asparatate, glutamate, lysine, arginine, histidine, alanine, valine, leucine, isoleucine, phenylalanine, methionine, tryptophane, proline, serine, threonine, asparagine, glutamine, glycine, cysteine, and tyrosine) and lipids. Any genus or species of the invention may be included or excluded from the embodiments of the invention.

In a first aspect of the invention, a water-soluble uncharged surface adsorbing polymer for surface modifications of test tubes, multi-well plates, pipettes, pipette tips, microtiter plates, reaction wells, microchannels, microfluidic apparati, capillaries and microcentrifuge tubes etc., particularly for use in microfluidic devices and plastic devices such as microtiter plates is provided. Preferably, the solubility of the polymer, in contrast to BSA, does not change dramatically within the temperature range important for biological reactions (i.e., 37–94° C.). The polymer may be a homopolymer or a copolymer. The surface modification of channels in microfluidic devices renders such microdevices suitable for chemical or biochemical reactions. While any suitable surface adsorbing polymer may be used, preferred polymers include for example, polyacrylamides such as polyacrylamide (PAM), N-isopropylacrylamide (NIPAM) and polydimethylacrylamide (PDMA), other polymers, such as propylene glycol (PG) and ethylene glycol (EG), and polyglycols including polypropylene glycols (PPG) and polyethylene glycols (PEG). Other preferred polymers are propylene oxide (PO) and ethylene oxide (EO), and polyoxides including polypropylene oxides (PPO) and polyethylene oxides (PEO). Still other preferred polymers are polydimethylsiloxane (PDMS) or polyvinylpyrolidone. Most preferred polymers are block copolymers of the polymers listed herein, including for example block copolymers of PPG and PEG and PAM and NIPAM and PDMS, and further including block copolymers such as polyacrylamide-block-N-isopropylacrylamide (PAM-NIPAM) and polydimethylsiloxane-block-polyethyleneglycol (PDMS-PEG). The molecular weight of the surface adsorbing polymers can be important to the stability of the adsorbed polymer layer. While polymers of any molecular weight can be chosen, polymers are preferably of molecular weight of greater than $1 \times 10^6$ daltons, improving the stability of the adsorbed polymer layer at high temperatures. Polymers having a molecular weight of about $1 \times 10^6$ daltons and greater are particularly useful for biological applications, particularly reactions involving temperature cycling. Polymers are further described herein.

As used herein, the term polymer refers to a molecule composed of smaller monomeric subunits covalently linked together. The term polymer encompasses the term homopolymer, which refers to a polymer made of only one type of monomer, as well as the term copolymer, which refers to a polymer made up of two or more types of monomer.

The polymer can be introduced to a surface as a polymer solution, preferably as an additive in a fluid sample, e.g., reaction mixture. The polymer can be introduced alone in a solvent, or in combination with, for example a biomolecule, chemical or cell. The useful concentration of polymer for surface modifications is preferably in the range between about 0.001% to about 5% (weight/volume). A preferred concentration is about 0.1% (weight/volume). As described further herein in the section titled "Polymers and Solutions", it will be appreciated that polymer concentration, polymer length and viscosity of the solution containing the polymer can be adapted to suit different channels and fluid operations.

The polymers of the invention have several advantages over previously used surface deactivation methods. Certain polymers of the invention, such as PDMA, are water-soluble in a temperature range important for biological reactions, while BSA denatures and becomes less polar (more hydrophobic) at high temperatures (>~60° C.). Polymers such as PDMA are also uncharged (although PDMA may become negatively charged upon hydrolysis at elevated temperatures in alkaline buffers) and chemically more simple molecules than BSA decreasing the probability for the non-specific interaction of the modified surface with reagents.

Apparati, devices and vessels, more specifically the substrates they are made of, can take any form, examples of which are further described herein. For example, plastics can be used to make tubular channels, such as in freestanding capillaries. Tubular channels or channels generally disposed in a thin substrate layer are used for example in liquid storage or distribution devices for use with microfluidics systems, such as capillary pipettors, capillaries used for transferring fluid samples to a microchannel or microfluidic device, or separate storage devices comprising storage channels and/or fluid reservoirs, including devices as described for introducing fluid samples into a microchannel in International Patent Publication No. WO 00/21666, the disclosure of which is incorporated herein by reference. While the microchannels can be used to carry out a wide variety of fluid operations, it will be appreciated that the polymers and methods related to the deactivation of channel surfaces are especially advantageous for fluid operations involving temperature cycling, such as PCR and single nucleotide primer extension, as well as general manipulation of proteins, particularly when the proteins are to be subjected to one or more different temperatures. In preferred aspects, microfluidic devices will thus comprise a temperature regulation means, particularly a means for cycling temperatures of the contents of a channel. Preferably, the microfluidic devices will have a fluid movement means involving the creation of a pressure gradient across one or more channels. Microfluidic devices, including related temperature regulation means, fluid movement means as well as fluid operations are further described herein.

Several different methods for adsorbing a polymer onto a surface are provided. Further description concerning principles of polymer adsorption are presented herein. In one example, the polymer solution is added to the fluid sample prior to adding the fluid sample to a device of the invention. In another example, a polymer solution, either in the presence or absence of a fluid sample, such as that comprising a test analyte or reagent, is moved through a channel such that the polymer adsorbs to the channel surface. Preferably, the movement of the polymer solution is affected by creating a pressure gradient, such as can be provided by a syringe, peristaltic pump and/or a pressurized gas. Once the channel is coated with the polymer, any number of fluid samples may be passed through the channel sequentially. Means for injection of the polymer solution, the fluids which are subject to the fluid operations, and fluid movement means are further described herein. The microfluidic devices that can be used according to the methods of the invention are also further described herein. It will be appreciated that a wide variety of channel substrates, channel geometries, and components for the storage, handling, injection and/or detection of fluid samples can be used according to the methods of the invention.

Any surface that has been treated with a polymer according to the invention may be regenerated with a fresh surface adsorbing polymer solution. The coating process described above may be repeated at any desired time by moving a polymer solution through the channel. The polymer solution can be moved through the channel at the same time (i.e., in the presence of) a fluid sample of interest, or can be moved through the channel before the running of further samples. In particularly preferred embodiments, the invention involves a dynamic coating method. The dynamic coating method involves regenerating the channel surface at regular intervals in order to maintain a consistent surface quality when a channel is used repeatedly. This is especially valuable for microfluidic applications where many samples are run sequentially in a channel.

As used herein, an individual fluid sample injected into a channel forms what is referred to as a fluid sample zone. Several fluid sample zones may be injected sequentially, for example. In certain embodiments, it is preferable to separate the fluid sample zones in order to prevent mixing of the zone contents by providing a fluid separating zone between fluid sample zones.

In a first example of the methods of the invention, one, two or more fluid sample zones are provided sequentially in a channel. In such an embodiment, the surface adsorbing polymer is provided in the fluid sample zone. The surface adsorbing polymer can be provided in each fluid sample zone, or only in certain fluid sample zones or at suitable intervals.

In other embodiments, the surface adsorbing polymer is provided in one, or in two or more fluid sample zones, but not in a fluid separating zone(s). In another embodiment, the surface adsorbing polymer is provided in one, or in two or more fluid separating zones, but not in a fluid sample zone(s). In another embodiment, the polymer is provided in at least one fluid separating zone, but is essentially absent from at least one fluid sample zone. In yet another embodiment, the polymer is provided in at least one fluid separating zone and in at least one fluid sample zone.

The surface adsorbing polymer can be included with a fluid sample and fed into a channel as a mixture. Alternatively, a surface adsorbing polymer solution and a fluid sample can be fed into a common channel through separate entry ports, or fed simultaneously through a common port. The fluid sample may comprise, for example, any test analyte, reagent, reaction mixture or biomolecule. The surface adsorbing polymer can thus be used as an additive in a reaction mixture. After injection, the solution can then be moved through the channel, preferably in a continuous flow mode, such that the surface adsorbing polymer solution will regenerate the channel surface.

The surface adsorbing polymer concentration can be optimized according to a specific fluid operation, or preferably a specific biochemical reaction. In general, the polymer concentration should be minimized so that the viscosity of the fluid medium in the channel does not increase dramatically and that the amount of the surface adsorbing polymer used is not excessive. To select the optimal polymer concentration, biochemical reactions can be performed in a microfluidic device with variable polymer concentrations. For example, using a protocol as shown in Example 2, an optimal polymer concentration can be easily selected by determining polymer concentrations which provide an acceptable product quality or yield.

The invention also provides methods of carrying out various fluid manipulations in a channel coated with a surface adsorbing polymer of the invention. In the dynamic coating methods, performing fluid operations, particularly biochemical reactions, involves providing a fluid comprising a test analyte or reagent, preferably a biomolecule, reaction mixture or protein, to a channel in the presence of a surface adsorbing polymer. When sequential fluid operations are performed in the same channel, the surface adsorbing polymer does not have to be added to each fluid operation or to each fluid unit, but may be added only to every second, third, fourth, fifth, tenth, twentieth fluid operation, for example.

A wide variety of fluid operations can therefore be carried out. Methods for carrying out fluid operations include carrying out reactions, incubations, separations, dilutions, titrations, purifications, detections, drug screening assays, mixing, binding assays, measuring assays (e.g., measurement of kinetics) as well as any operation generally involving a large number of successive manipulations, and any fluid manipulation where the fluid sample comprises a test analyte or reagent, particularly when the test analyte or reagent is a biomolecule, and more preferably where the test analyte or reagent is a nucleic acid or a amino acid.

1. Polymers & Solutions

The invention provides a water-soluble uncharged surface adsorbing polymer for surface modifications of channels, such as freestanding capillary channels and in microfluidics devices. Any suitable polymer may be used, preferably a polymer for which solubility does not change dramatically within a temperature range relevant for biological reactions (e.g., between about 20–100° C. or more preferably between about 37–94° C.). Preferably, a silica adsorbing polymer is specified. Preferably, the polymer is from a family of polyacrylamides, such as polyacrylamide (PAM), N-isopropylacrylamide (NIPAM) and polydimethylacrylamide (PDMA). In other preferred embodiments, other polymers, such as propylene glycol (PG) and ethylene glycol (EG), and polyglycols including polypropylene glycols (PPG) and polyethylene glycols (PEG) may be used as surface adsorbing polymers. In still other preferred embodiments, other polymers, such as propylene oxide (PO) and ethylene oxide (EO), and polyoxides including polypropylene oxides (PPO) and polyethylene oxides (PEO) may be used as surface adsorbing polymers. In further preferred embodiments, the surface adsorbing polymer is polydimethylsiloxane (PDMS) or polyvinylpyrolidone. In most preferred embodiments, block copolymers of the polymers listed herein are used, including for example block copolymers of PPG and PEG and PAM and NIPAM and PDMS, and further including block copolymers such as polyacrylamide-block-N-isopropylacrylamide (PAM-NIPAM), polydimethylsiloxane-block-polyethyleneglycol (PDMSPEG).

Synthesis of polymers can be carried out according to methods known in the art. Examples of suitable polymer synthesis methods are described in Odian, Principles of Polymerization, 3$^{rd}$ Edition (John Wiley, NY, 1991), the disclosure of which is incorporated herein by reference in its entirety.

A preferred polymer, PDMA, can be synthesized according to well known methods. U.S. Pat. No. 5,567,292, the disclosure of which is incorporated herein by reference, provides one example of a synthesis method of PDMA. PDMA may also be synthesized as described below in Example 1, and as described in Viovy, J.-L., Hourdet, D., Sudor, J., French Patent No. 98 16676, the disclosure of which is incorporated herein by reference.

Block copolymers of PPG and PEG (PPG-PEG-PPG and PEG-PPG-PEG block copolymers) or EO and PO are commercially available. SYNPERONIC, PLURONIC® and PLURONIC®R block copolymers (EO-PO-EO and PO-EO-PO) are available for example from BASF, Ludwigshafen Germany.

As discussed herein, several different methods for adsorbing a polymer onto a surface are provided. In one example, a polymer solution, either in the presence or absence of a fluid sample is moved through a channel such that the polymer adsorbs to the channel surface. The polymer concentration is typically minimized so that the viscosity of the fluid medium in the channel does not increase dramatically and that the amount of the surface adsorbing polymer used is not excessive. In the case when the polymer solution comprises a test analyte or reagent, it is appreciated that consideration should be given to the influence of the viscosity of polymer solutions on the kinetics of any possible biological reaction. Preferably, the viscosity of the polymer solution is selected such that it does not affect the biological reaction.

Polymer Properties

A polymer molecule (such as PDMA, DNA, etc.) behaves as a random coil with its radius of gyration $R_g$ proportional to the square root of the chain's contour length L (or number of monomers N): $L=N.l$ and $R_g \sim L^{1/2}.l^{1/2}$ or $R \sim N^{1/2}.l$, where l is the length of a one monomer. Consequently, a polymer molecule appears much smaller in size than it would be if entirely stretched.

A polymer solution, in general, at a given temperature and in a given solvent, can be characterized by the polymer mass concentration C, its average molecular mass $M_w$, and by the viscosity of the polymer solution η.

With respect to the polymer solution's concentration one can recognize three different regimes: (a) dilute; (b) semi-dilute; and (c) concentrated. In the dilute regime, polymer chains are isolated from each other, in good solvents where polymer/solvent interactions are preferable. As the concentration of a polymer solution is increased above a critical concentration (C*) polymer chains become entangled. The dilute (C<C*) and semi-dilute (C>C*) regimes, with the crossover between them (C~C*) are shown in FIG. 1. Clearly, the threshold (critical concentration) is not sharp but it is defined as a region of crossover between the two regimes. From scaling arguments, C* is expected to be comparable with the local concentration inside a single polymer coil.

In a good solvent this implies:

$$C^* \sim N/R_g^3 = a^{-3} N^{1-3\gamma} = a^{-3} N^{-4/5} \quad (1)$$

where N is the number of monomers in a polymer coil, $R_g^3$ is the volume of a polymer coil and α is the polymer's persistence length. The persistence length of a polymer molecule defines its flexibility. The physical meaning of the persistence length is that a memory of a chain direction is retained only on length scales shorter than l (the memory of a chain direction is lost on the length scales greater than l). In more practical terms, the overlap threshold concentration is related to the intrinsic viscosity of a polymer solution as:

$$C^*=1.5/[\eta] \quad (2)$$

The intrinsic viscosity of a polymer solution is obtained by extrapolating a reduced viscosity $\eta_{red}=(\eta-\eta_s)/\eta_s$ to zero polymer concentration (Sun S. F., Physical Chemistry of Macromolecules, Wiley-Interscience, John Wiley and sons, Inc., New York, 1994). Intrinsic viscosity of a polymer solution is also related to the polymer's molecular weight through the Mark-Houwink relation: $[\eta]=KM_w^a$, where K and α are the Mark-Houwink coefficients.

For C<C*, the polymer solution can be regarded as a diluted system of polymer coils. The polymer coils behave as hard spheres. This comes from the fact that when two coils are forced to overlap in a good solvent, each polymer/polymer contact brings an energy of order $k_B T$ (where $k_B$ is the Boltzman constant and T is temperature). Since many contacts must occur between overlapped polymer coils, the overall overlap energy is several $k_B T$, entering the Boltzman exponential very small and, consequently, the polymer coils do not overlap each other.

In the semi-dilute regime (C>C*), the polymer coils overlap with each other and the polymer solutions behaves as a dynamical network. All thermodynamic properties (e.g., local energies, entropies, etc.) of such solutions are controlled only by the solution's concentration C and not by the length of a polymer chain N. The important length scale of such dynamical networks is an average distance between different polymer chains (an average mesh size). The dynamic mesh size S of a polymer solution can be derived from scaling arguments for C~C* and is inversely proportional to the polymer solution concentration $C^\theta$ (only when C>C*):

$$S \sim R_g \, (C^*/C)^{3/4} \qquad (3)$$

Diffusion coefficients of molecules are related to their size, the viscosity of a medium in which they diffuse and the temperature through the Einstein-Stokes relationship:

$$D = k_B T / 6\pi \eta R \qquad (4)$$

where D is a molecular diffusion coefficient, $\eta$ is the viscosity of a polymer solution and R is the molecular radius. It is evident that diffusion coefficients of biological molecules will decrease with an increase in solution's viscosity. The viscosity of polymer solutions $\eta$ in the dilute regime (C<C*) depends linearly on the polymer concentration ($\eta \sim C$) but this dependence becomes non-linear (i.e., $\eta \sim C^\alpha$ where $\alpha > 1$ in semi-dilute regimes (C>C*). Thus, diffusion of biological reagents can be affected dramatically with a small change in the polymer concentration in semi-dilute regimes (C>C*).

$$D = k_B T / 6\pi C^\alpha R \qquad (5)$$

Polymer Adsorption

Preferably, the bulk concentration of a polymer solution used for surface modification that comprises a mix of reagents is below the overlap threshold concentration C*. The overlap threshold concentration decreases with an increasing polymer size, suggesting that when large polymers ($M_w > 10^6$) are used for surface modifications low concentrated polymer solutions ($C_{bulk} < 1\%$) should be employed.

The polymer adsorption onto surfaces happens if the interaction between the polymer and the surface is more favorable than that of the solvent with the surface. Therefore, even polymers that are highly soluble in a solvent (e.g., in water) can adsorb onto a solid substrate, if the solid substrate "prefers" to interact with the polymer instead of the solvent molecules. A simple way to predict if a polymer dissolved in a given solvent is going to adsorb onto a surface is to measure the surface tension of a pure solvent $\gamma_s$ (e.g. water) and a pure polymer $\gamma_p$. When $\gamma_s > \gamma_p$ the polymer is expected to adsorb onto a surface when dissolved in the particular solvent. There are two main factors determining polymer adsorption onto a surface. A first factor is a solid substrate/monomer (a smallest part of a polymer) interaction (an energy that favors the polymer's adsorption). A second factor is the reduction of conformational states of the polymer at the substrate (decrease of the chain's entropy). This is due to the impenetrability of the substrate for monomers and it is the energy that tries to keep the polymer away from a surface. In addition, repulsive monomer/monomer interactions in a good solvent favor pushing the polymer away from a surface (i.e., excluded volume interactions tend to increase the thickness of an adsorbed polymer layers in good solvents). The strength of the polymer's adsorption is thus given by the ratio of attractive and repulsive forces.

The adsorbed polymer layers are stable when built from long polymers. For instance, polymer/surface interactions are relatively weak (a fraction of $k_B T$ unit) in adsorbed polymer layers. However, due to the large number of segments interacting with a surface, which may be more than 10% of the total number of segments/monomers in a polymer, the total adsorption energy per a single polymer molecule can be very large, reaching several $k_B T$ units and thus rendering polymer adsorption virtually irreversible, particularly when long polymers are employed. In addition, long polymers adsorbed on surfaces have more degree of freedom than short ones resulting in more stable surface coatings. Nevertheless, it has been shown in experiments (Thies, C., J. Phys. Chem. 70 (1976) 3783, and Cohen-Stuart, J. et al., J. Polymer Sci. (Phys.), 18 (1980) 559) that polymers adsorbed on surfaces may be exchanged with polymers in bulk solution. The first observation showed that short polymers adsorbed on a surface can be replaced by large polymers if present in the bulk solution, and also suggests that adsorbed polymer layers made from large polymers are more stable than those built from short polymers. Consequently, Phefferkorn, E., et al. (J. Polymer Sci. (Phys.), 23 (1985) 1997) showed that the exchange between polymer chains adsorbed on a surface and identical chains in the bulk solution is governed by second order kinetics:

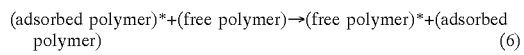

(adsorbed polymer)*+(free polymer)→(free polymer)*+(adsorbed polymer)　(6)

suggesting that the de-sorption rate is proportional to the concentration of polymer chains on the surface C* and in the bulk solution C ($-dC^*/dt = kC^*C$, where k is a constant).

A significant property of an adsorbed polymer layer is the strong repulsive interaction between neighbor polymer molecules. This means that when the number of polymers on the surface increases, the attractive energy between a surface (with polymers) and the adsorbing polymer is decreasing. In other words, the "quality" of the surface is being changed by the adsorbing polymers, thus the surface quality is not the same for the first polymer that adsorbs on a surface and for the $n^{th}$ polymer molecule. There exists a finite (equilibrium) coverage (concentration, $C_e$ for a surface by polymer chains. When more polymers adsorb on a surface than is given by the equilibrium coverage, the free energy of these molecules becomes higher than the free energy of polymers in bulk solution and they quickly de-sorb. In other words, there is a restoring force that keeps the equilibrium coverage constant. The condition of nearly constant equilibrium coverage is called the saturation condition. The saturation condition states that polymer molecules can escape from an adsorbed layer only when polymers from bulk solution immediately replace them, in order to maintain constant $C_e$.

Figure 2:
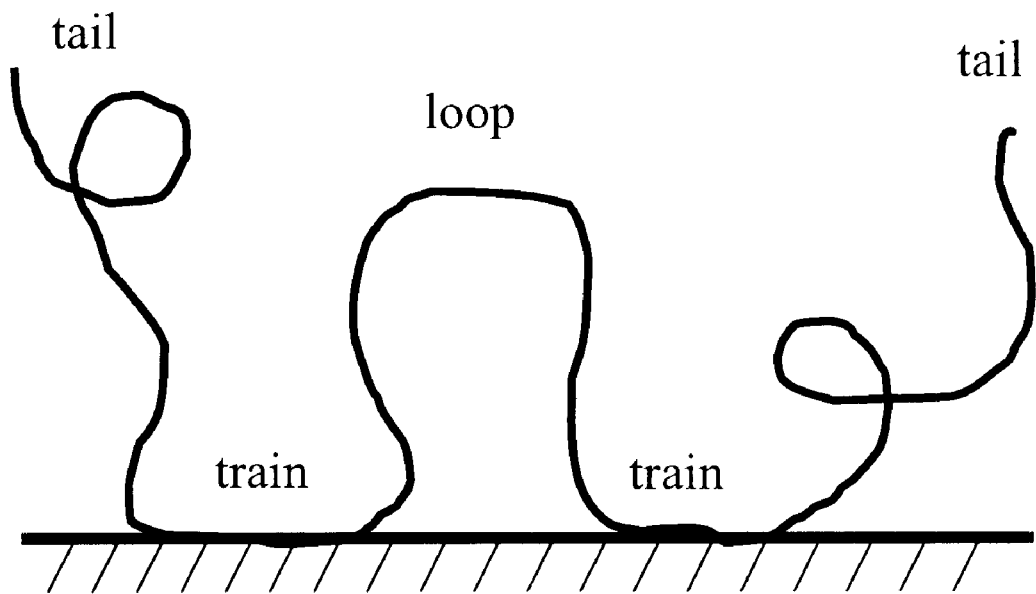
FIG. 2 shows a surface adsorbing homopolymer adsorbed onto a solid substrate in tail-loop-train conformation.
Figure 3:
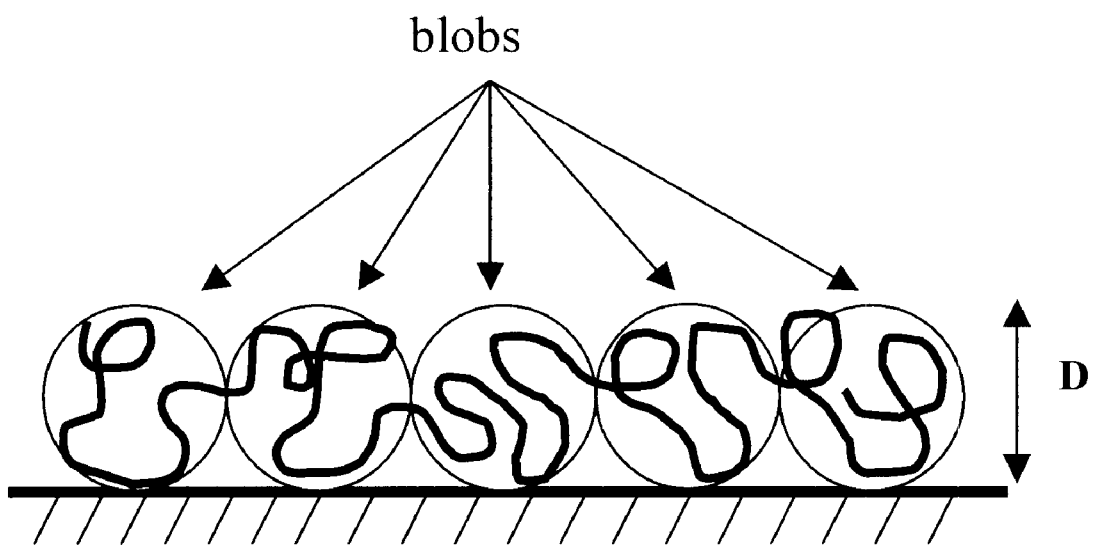
FIG. 3 shows the conformation of an adsorbed homopolymer adsorbed on a channel surface.

The single polymer adsorbed onto a solid substrate is described in terms of tail-loop-train conformation, represented in FIG. 2. The polymer segments belonging to the trains are attached to a surface while the segments of tails and loops are in a solution. The conformation of an adsorbed polymer is unperturbed on a length of the order of the thickness (D) of the adsorbed layer. On much large length scales, the polymer is broken into decorrelated polymer blobs, as shown in FIG. 3.

Figure 4:
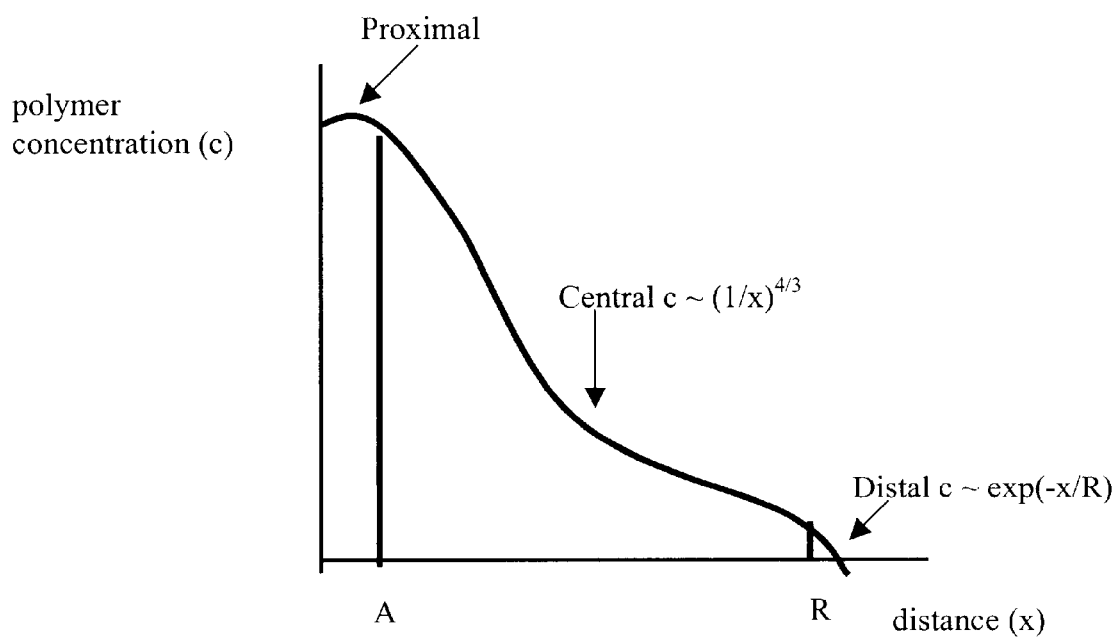
FIG. 4 shows polymer concentration (c) as a function of the polymer's distance (x) from the surface onto which it is adsorbed. The adsorbed polymers form a layer that is made up of a proximal, a central and a distal region having different sensitivities to the details of the polymer-surface interactions.

The adsorbed polymers form a layer that is made up of three regions: proximal (very sensitive to the details of the polymer-solid interactions), central (this layer is self-similar, i.e., concentration vs. distance (normal to the surface) dependence is governed by a power law) and distal (controlled by a few large loops and tails), as shown in FIG. 4. The polymer layer (FIG. 4) that is formed on a surface prevents interactions and, consequently, adsorption of biological molecules with/to a surface through a steric (entropic) repulsion.

The reader will appreciate that the average molecular weight of the polymer may vary, depending on the applications envisioned for the microchannel. In certain embodiments, polymer solutions have an average molecular weight of at least $1 \times 10^3$, $5 \times 10^3$, $1 \times 10^4$, $5 \times 10^4$, $1 \times 10^5$, $5 \times 10^5$, $1 \times 10^6$ or $5 \times 10^6$ daltons. In preferred embodiments, the molecular weight of the surface adsorbing polymers is superior to $1 \times 10^6$ daltons, thus improving the stability of the adsorbed polymer due to increase in chain's entropy (randomness) on the surface as compared to short polymer molecules ($<1 \times 10^6$ daltons). The increased stability of the adsorbed polymer layers built from long polymers is important for protocols with changing/cycling temperature (e.g., PCR and MIS reactions). In general, polymers can desorb from a surface when temperature is increased due to an increased thermal (randomizing) energy of the system.

As further described herein, the surface adsorbing molecule, preferably a polymer listed herein, may be provided together with a sample, a test analyte, or preferably with a biomolecule, and preferably as an additive to a reaction mixture. In other embodiments, the surface adsorbing molecule is provided in a solution essentially in the absence of a particular sample, test analyte, biomolecule or reaction mixture, preferably to regenerate a surface between test analytes in the same microchannel. A polymer solution will generally also comprises a suitable buffer, but this is not a requirement.

Preferably, the concentration of this polymer in solution for surface modifications is in the range of between about 0.001% to about 5% (weight/volume).

The surface adsorbing quality of a polymer can be determined according to well known means. The total surface coverage by a polymer (number of monomers/cm² of surface) and the thickness of the adsorbed polymer layer can easily be probed by hydrodynamic measurements (de Gennes, P. G., Advances in Colloid and Interface Sci. 27:189–209 (1987)) or by elipsometry (Azzam, R., Bashara, N., Ellipsometry and Polarized Light, North Holland, 1977; Charmet, J. C., de Gennes, P. G., J. Opt. Soc. Am. 73: 1777 (1983), the disclosures of which are all incorporated herein in their entireties.

In hydrodynamic experiments, a colloidal particle of radius R that moves in the polymer layer with a velocity V will encounter a friction force $(6\pi\eta(R+e_H)V)$, where $e_H$ is a hydrodynamic thickness of the adsorbed polymer layer. In elipsometric experiments, the residual reflectance of the in-plane polarized light at the Brewster angle depends on the total surface coverage (i.e., the reflectance coefficient vanishes when there is no polymer adsorbed on a surface). With elipsometry, it is possible to determine the thickness of the film in the range of 1–1000 Angströms. More elaborated techniques for studies of polymer layers on surfaces employ, e.g., evanescent waves (Allain, C., et al., Phys. Rev. Lett. 49: 1694 (1982), the disclosure of which is incorporated herein by reference) or neutron scattering (Barnett, K. et al., The effects of Polymers on Dispersion Stability, Tadros, J., ed., Academic Press, 1982, the disclosure of which is incorporated herein by reference). Additionally, the viscous and elastic properties of polymer layers adsorbed on surfaces can be studied by surface force apparatus (SFA) [Israelachvili, J. N. et al., Faraday Trans. I, 74: 975 (1978); Klein, J. et al., Nature 300: 429 (1982); Klein, J., et al., Nature 308: 836 (1984); and Dhinijwala, A., et al., Macromolecules 30: 1079–1085 (1997)]. The disclosures of each of the above listed references are incorporated herein by reference.

2. Polymer Adsorption in Dynamic Mode

In one embodiment, a channel is contacted with a polymer solution prior to contacting the channel with a test analyte or reagent. For example, a polymer solution is moved through a channel such that the polymer adsorbs to the channel surface. Preferably, the solution is moved by creating a pressure gradient across the channel, such as can be created through the use of a pressure or vacuum based injection syringe or another suitable fluid delivery means. Alternatively, a channel, particularly a channel such as in freestanding capillaries, can be placed directly into a polymer solution; the polymer solution will then wick into the channel by capillarity, or may be drawn into the channel by pressure gradient.

Once the channel is coated with the polymer, a solution comprising a fluid sample of interest may be introduced to the channel, for example as part of any desired fluid operation.

Any suitable surface onto which a polymer coating has been adsorbed may be regenerated or maintained with a fresh surface-adsorbing polymer coating according to the invention. The coating process described above may be repeated at a desired time by moving a polymer solution through the channel. Thus, in particularly preferred embodiments, the invention involves a dynamic coating method. Using the dynamic coating method, a channel surface can be regenerated or maintained during use in order to provide a consistent surface quality when a channel is used multiple times, i.e. running sequential fluid operations in a channel, also referred to as running in series.

In one embodiment, the surface adsorbing polymer is used as an additive to a fluid comprising a fluid sample of interest. A surface adsorbing polymer is added to each fluid volume introduced to the channel, or to every $2^{nd}$, $3^{rd}$, $4^{th}$, $5^{th}$, $6^{th}$, $8^{th}$, $10^{th}$, $20^{th}$, $50^{th}$ or $100^{th}$ fluid. For example, in an exemplary process of the invention, the surface adsorbing polymer is added to a PCR mixture, to an exonuclease/shrimp alkaline phosphatase (EXO/SAP) purification mixture, and to a microsequencing (MIS) mixture. This surface adsorbing polymer adsorbs onto a surface and forms a polymer layer at a solid/liquid interface. The concentration of polymer in the adsorbed layer on a surface reaches an equilibrium value. The concentration of polymer for surface modifications will typically be in the range of about 0.001% to about 5% (weight/volume). Preferably, the polymer concentration is in the range between about 0.01% to about 1% (weight/volume). However, it will be appreciated that the equilibrium concentration of the adsorbed polymer depends, among other factors, on temperature and on the surface material of the channel, and that the concentration of polymer in solution can thus be further optimized according to the particular application.

As described above, a volume of fluid introduced to a channel can be referred to as a fluid zone, as in the case when injected into a channel sequentially. Fluid zones may comprise or consist of any suitable fluid, including but not limited to for example water or a buffer. A fluid zone may also comprise a sample. Fluid zones, particularly fluid zones comprising samples (fluid sample zones), can be separated by separating fluid zones so as to decrease diffusion of samples, or may simply be introduced one after another such that some diffusion occurs. In preferred embodiments, fluid operations are carried out sequentially in a channel.

Preferably, at least 2, 3, 5, 10, 15, 20, 30, 50, 100, 200 or 1000 sequential fluid zones are provided in a channel. The surface adsorbing polymer may thus be provided in at least one fluid zone comprising a sample, or in at least one fluid separating zone. Preferably, the surface adsorbing polymer is present in at least 2, 3, 5, 10, 15, 20, 30, 50, 100, 200 or 1000 samples or fluid sample zones, or in at least 2, 3, 5, 10, 15, 20, 30, 50, 100, 200 or 1000 fluid separating zones. In other embodiments, the surface adsorbing polymer is provided in at least 1, 2, 3, 5, 10, 15, 20, 30, 50, 100, 200 or 1000 fluid separating zones and is absent from at least one, or all, of the fluid sample zones. Alternatively, the surface adsorbing polymer is provided in both a fluid sample zone and a fluid separating zone. Preferably, the surface adsorbing polymer is present in at least 1, 2, 3, 5, 10, 15, 20, 30, 50, 100, 200 or 1000 fluid sample zones and in at least 1, 2, 3, 5, 10, 15, 20, 30, 50, 100, 200 or 1000 fluid separating zones. Preferably, the surface adsorbing polymer is present in all fluid separating zones.

It will be appreciated that a channel may be pretreated with a polymer solution (e.g. channel is contacted with a polymer solution prior to contacting the channel with a test analyte or reagent). Alternately, fluid operations comprising fluid samples to which polymer has been added can be carried out without pretreatment of the channel with a polymer solution.

In one example, the channels (few hundred of µm size range) of a silicon microfluidic device are filled with a solution of PDMA (~10 µl) of an optimized concentration (e.g., 0.1% at present) and equilibrated for 10 min. Subsequently, alternating zones of fluid samples, that contain PDMA (0.1% weight/volume), and non-polar fluid separating zones, are pushed through a device. Each fluid sample zone contains biological components (i.e., protein sample, PCR, EXO/SAP or MIS reaction mixture) and PDMA. Thus, the surface of a microfluidic device is pre-coated prior to the samples containing the biological components entering the system, and then PDMA is provided in each fluid zone containing a biological sample in order to regenerate the channel surface for each reaction.

It will be appreciated that the surface adsorbing polymer can be introduced to the channel by any suitable means. The polymer can be introduced as a mixture with a sample, or separately through a common or separate entry ports.

3. Microfluidic Devices

The microfluidics substrate can take many different forms. The substrate may be a thin substrate layer surrounding a channel, as in tubular substrates, such as currently available polymer or fused silica capillaries. In other embodiments, substrates are in a planar substrate in which one or multiple channels are disposed. Typically, grooves in the planar substrate are fabricated, and are closed with a cover element or a second substrate containing matching grooves. In preferred embodiments, the microfluidic devices comprise such integrated microchannel systems, wherein multiple channels are disposed in a single microfluidics substrate.

Substrates can be any suitable material. Preferred substrate materials are silica based substrates such as silica, silicon, glass, quartz. Suitable substrate materials also include metals as well as polymers such as plastics, including polystyrene, polypropylene, polymethyl methacrylate, polyvinyl chloride, polyethylene, polycarbonate, polysulfone, fluoropolymers, polyamides, polydimethylsiloxanes, polyurethane, polysulfone, polytetrafluoroethylene (Teflon ™), and elastomers for example. Other suitable substrates are known in the art and can also be used. Substrates may have unmodified surfaces, or may be treated so as to modify the properties of the surface; for example, a silanization step can be carried out on silicon substrates prior to use in fluid operations.

Substrates with microchannels disposed therein can be used in a variety of applications, as further described herein. For example, microchannels may be used for the movement of fluids in a reaction channel, for the movement of fluids to a reaction channel or chamber in a microfluidics device, in a sample or reagent distribution means (e.g. for the movement of fluids to or from a device), or for the storage of fluids to be used in a device (e.g. a microfluidics device).

One example of a microfluidics device that can be used in accordance with the present invention is shown in copending U.S. patent application titled "Integration of biochemical protocols in a continuous flow microfluidic device" and PCT application no. PCT/IB00/01137, both filed Jul. 28, 2000.

Channels may be of any suitable geometry, and may be disposed in a microfluidic device in any suitable format. Channels also can be any of a variety of different shapes in cross-section, including tubular channels, rectangular channels, rhomboid channels, hemispherical channels or the like, or even more arbitrary shapes, such as may result from less precise fabrication techniques, e.g., laser ablation. Typically, the shape of a capillary channel will vary depending upon the substrate type used and the method of fabrication. For example, in typical fused silica capillaries, the capillary channel will be tubular. In systems employing planar substrates, on the other hand, channels will typically comprise either a rhomboid, rectangular or hemispherical cross sectional shape, depending upon the substrate material and method of fabrication of the channels.

A variety of manufacturing techniques are well known in the art for producing microfabricated channel systems. For example, where such devices utilize substrates commonly found in the semiconductor industry, manufacturing methods regularly employed in those industries are readily applicable, e.g., photolithography, wet chemical etching, chemical vapor deposition, sputtering, electroforming, etc. Similarly, methods of fabricating such devices in polymeric substrates are also readily available, including injection molding, embossing, laser ablation, LIGA techniques and the like. Other useful fabrication techniques include lamination or layering techniques, used to provide intermediate microscale structures to define elements of a particular microscale device. Techniques are also described in Sorab K. Ghandi, VLSI Principles: Silicon and Gallium Arsenide, NY, Wiley.

Typically, channels will have an internal cross-sectional dimension, e.g., width, depth, or diameter, of between about 1 µm and about 3 mm, with most such channels having a cross-sectional dimension in the range of from about 10 µm to about 1000 µm.

In particularly preferred aspects, planar microfluidic substrates employing multiple integrated channels are used. The planar microfluidic devices generally employ an integrated channel network fabricated into the surface of a planar substrate. A second substrate, which may or may not have complementary channels formed therein, is overlaid on the surface of the first to cover and seal the channels, thereby defining the channels.

Channels may be arranged such that channels communicate at one or more intersections, as in embodiments where fluid reservoirs or feed channels communicate to a primary fluid operation, or reaction, channel, as in U.S. Pat. No. 5,858,195, incorporated herein by reference. Alternatively, channels may be arranged so that they do not communicate with other channels. Channels may be formed essentially in a straight line, or have turns, such as in serpentine channels. In certain embodiments, a large number of channels are arranged in parallel, in order to carry out a large number of parallel analyses simultaneously.

A microfluidics device may also comprise reaction wells. For example, a fluid sample may be moved through a channel treated according to the invention to a reaction well, and a reaction is then carried out in the reaction well. The fluid can then be moved further, egg to an outlet, further reaction chamber, storage reservoir, etc.

As used herein, a fluid movement system is a system for moving or flowing fluids through a microchannel. Known fluid movement systems include pressure or vacuum based systems, electrokinetic, electroosmotic and electro-hydrodynamic systems (WO 98/45481 and U.S. Pat. No. 6,046,056) as well as heat gradient movement means (U.S. Pat. No. 6,057,149). The disclosures of the above references are incorporated herein by reference. In preferred embodiments, pressure or vacuum based fluid movement means are used, which can be effected by a wide range of mechanisms, including the use of micropumps, microvalves and syringes. Fluid movement means may effect one or several successive fluid movements, or may effect the movement of fluids in continuous flow through a channel.

Due to the stability of the polymer coating at high temperatures and at changing temperature conditions, the invention is also advantageously carried out in a microfluidics device having a temperature regulation means which is capable of heating and/or cooling the contents of a channel.

Optionally, the subject device may also comprise a wide range of additional components, such as an interface means (e.g. syringe) for assisting in the introduction of a fluid sample into a channel, another microfluidic device, reservoir, fluid storage, distribution device, etc. An example of an apparatus for introducing fluid samples into a microchannel is described in International Patent Publication No. WO 00/21666, the disclosure of which is incorporated herein by reference. The subject devices may optionally have one or more reservoirs for the storage of fluid components such as reagents, test analytes, etc. The device may include a detection zone at which a signal from a sample or biochemical reaction may be monitored, and optionally detection means for measuring a signal.

4. Fluid Operations

The methods of the invention, and the polymer-coated channels and microfluidic devices comprising the channels can be used advantageously in a wide range of fluid operations.

Fluid operations include among other operations mixing, carrying out reactions, incubations, separations, dilutions, titrations, purifications, detections, mixing, binding assays, measuring assays (e.g., measurement of kinetics) and drug screening assays. Fluid operations also generally include subjecting a fluid to one or several different temperatures. Fluid operations also include operations generally involving a large number of successive manipulations. Fluid operations also include any fluid manipulation where the fluid comprises a sample, such as a test analyte or reagent, particularly when the test analyte or a reagent is a biomolecule, and more preferably where the test analyte or reagent is a nucleic acid or a amino acid. Several examples of fluid operations that can be carried out in microchannels are described in International Patent Publication No. WO 98/45481, the disclosure of which is incorporated herein by reference in its entirety. Preferred examples of fluid operations also involve the manipulation of proteins in a channel, such as in the field of proteomics, exemplary applications of which are presented in copending U.S. patent application titled "Integration of biochemical protocols in a continuous flow microfluidic device" and PCT application no. PCT/IB00/01 137, both filed Jul. 28, 2000.

In one example, microfluidic devices are used to perform fluid manipulations of reagents, such as for the combination of reagents for a reaction mixture, the apportionment of reagents into multiple compositions. In one aspect, dilutions of samples or reagents in small volumes can be carried out, particularly dilutions carried out in serial fashion. In another example, titrations can be carried out, such as for the titration of an assay for assay normalization. For example, the various components of an assay can be titrated in order to define the dynamic range where the individual components are in the range that allows quantitative results to be obtained. Not limited to reagents and test analytes, the microfluidic devices can also be used for the manipulation of cells, as described in International Patent Publication No. WO 99/67639, the disclosure of which is incorporated herein by reference. The channels and microfluidic devices can also be used in drug screening assays, which generally involve the mixing of several components, incubation and the testing of an outcome in a detection step. It will be appreciated that any desired reagent or test analyte can be used; examples include but are not limited to nucleic acids, amino acids, lipids, chemical compounds, and more specifically receptors or antibodies and their ligands, cells and growth factors and growth inhibitors, and enzymes and substrates. The microfluidic devices can also be used for the detection of any desired test analyte, such as in diagnostic assays. For example, a test analyte such as a nucleic acid or protein sample can be passed through a channel where a detection apparatus determines the presence or absence of a particular signal. A microfluidic device may further comprise a channel or a means for separation of components, such as by electrophoresis. In certain embodiments, a surface adsorbing polymer is provided in the presence of a separation matrix. In other embodiments, the surface adsorbing polymer is provided in a solution essentially in the absence of a separation matrix. The surface adsorbing polymer may also be provided in the presence or absence in said channel of free particles (e.g. silicon) to which the surface adsorbing polymer is capable of binding.

It will also be appreciated that the channels and microfluidic devices of the invention are advantageous for many types of biochemical reactions. Particularly because the surface adsorbing polymers coatings of the invention are stable at the higher temperatures needed for many reactions, and because the coatings are stable across the range of temperatures encountered in thermocycling reactions, the invention is well suited for reactions such as nucleic acid amplification and primer extension reactions such as sequencing or various genotyping methods. The devices and processes in accordance with the invention make it possible to carry out, in continuous flow, biochemical protocols which include a step with thermal cycling. The invention is particularly well suited for carrying polymerase chain reaction (PCR), which is widely used in genetic analysis.

The invention, which can be used in genetic analysis, can also be used, however, for numerous protocols in the domain of biochemistry and of molecular biology. Thus, in a preferred embodiment, the invention comprises a method of conducting a biochemical reaction, wherein a reaction mixture is formed or provided in a channel coated with a surface adsorbing polymer, and thermocycling is carried out on said reaction mixture. Examples of preferred protocols which require temperature cycling and are derived from the PCR (Polymerase Chain Reaction) include RT-PCR, allele-specific PCR and TaqMan PCR [Molecular Cloning to Genetic Engineering, White, B.A. Ed. in *Methods in Molecular Biology* 67: Humana Press, Totowa (1997) and the publication entitled "PCR Methods and Applications", Cold Spring Harbor Laboratory Press(1991)]. LCR (Ligase Chain Reaction) techniques are also known, such as LCR, Gap LCR, RT-LCR, Asymmetric Gap LCR (RT-AGLCR) Marshall R. L. et al. (*PCR Methods and Applications* 4:80–84, 1994, the Oligonucleotide Ligation Assay (OLA) and PCR-OLA [Nikiforov, T., Anal Biochem 227(1):201–9 (1995)], [Marshall, R. L., PCR Methods Appl. 4(2):80–4 (1994)), (Nickerson, D. A. et al., Proc Natl Acad Sci USA.87(22):8923–7 (1990)]. Cyclic sequencing reactions using clones or PCR reactions are also known, as well as cyclic microsequencing (single nucleotide primer extension) reactions (Cohen, D., International Patent Publication No. WO 91/02087). The disclosures of each of the above listed references are incorporated herein by reference.

The most well known example of a temperature cycling reaction that can be carried out is nucleic acid amplification. A preferred method in the art is PCR, involving the use of one strand of a sample nucleic acid sequence to generate complements of the strand, which complements will further serve as nucleic acid templates for further reaction cycles. Generally, two primer sequences complementary to different ends of the target nucleic acid fragment to be generated are allowed to hybridize, or anneal, with the sample nucleic acid. When incubated in the presence of a polymerase enzyme and nucleoside triphosphates, the primers are extended along the target sequence in the direction of the opposite primer. The extended primers are then dissociated from the template nucleic acid by raising the temperature, and the process is repeated.

Other preferred reactions to be carried out according to the invention are sequencing reactions. Several different techniques for sequencing a nucleic acid are known, including the Sanger dideoxy chain termination method (Sanger et al., PNAS USA 74:5463–5467 (1977), the disclosure of which is incorporated herein by reference), sequencing by hybridization (Drmanac et al., U.S. Pat. No. 5,202,231, the disclosure of which is incorporated herein by reference), and the Maxam-Gilbert chemical degradation method. Sequencing in a microchannel is described in International Patent Publication No. WO 98/45481, the disclosure of which is incorporated herein by reference.

5. Polymer Adsorption on Plastic Surfaces

In one embodiment, the invention provides a method of decreasing adsorption of organic materials onto the surface of plastic apparati, comprising: (a) adding to a fluid sample a polymer comprised in an aqueous solution; and (b) performing one or more fluid operations in said plastic apparatus. Alternatively, the methods of the present invention may be applied to decrease adsorption of organic materials onto any other polar/non-polar interface (e.g., water/oil or water/air interfaces).

Methods of the invention are especially useful when performing fluid operations in small volumes. When working in small volumes, the interaction frequency of organic molecules with the interface (e.g., the liquid/solid interface between the surface of a plastic device and a reaction mixture, the liquid/liquid interface between oil and a reaction mixture, or a water/air interface) becomes non-negligible as a consequence of decreased distance over which molecules have to reach the interface. The intercation frequency scales with volumes, for a spherical geometry, as $V^{-1/3}$ and, in the same time, the interface-to-volume ratio (IVR) increases with deceasing volumes (IVR~$V^{-1}$). Consequently, the probability of organic molecule adsorption dramatically increases when working in small volumes. Thus the method of the present invention is preferably directed to perform fluid operations in volumes of less than any integer comprised between 20 and 0.1 $\mu$l.

Decreasing adsorption of organic materials onto the surface of plastic apparati using the method of the invention may be directed to increase the yield of biochemical reactions. Optimal quantity of polymer that should be added in a given reaction mixture of a given volume can be determined by a method comprising the steps of (i) adding to the reaction mixture different quantities of said polymer comprised in an aqueous solution; (ii) performing the reaction in a plastic device, and (iii) determining the quantity of polymer that should be added to obtain the highest yield.

Decreasing adsorption of organic materials onto the surface of plastic devices using the method of the invention may also be directed to decrease the contamination of subsequent fluid operations by organic molecules from the first fluid operation. Optimal quantity of polymer that should be added in a given fluid sample of a given volume can be determined by a method comprising: (a) adding to the first fluid sample different quantities of said polymer comprised in an aqueous solution; (b) performing the successive fluid operations in a plastic device, and (c) determining the quantity of polymer that should be added to obtain the lowest contamination of successive fluid operations by organic molecules from first fluid operation. In a preferred embodiment of the invention, said contamination comprises the undesired presence of deoxynucleotide triphosphates (dNTPs).

The methods of the invention can be used for decreasing adsorption of a wide range of organic molecules onto the surface of plastic devices. For example, organic molecules comprise nucleic acids, amino acids, amino acids, lipids and chemical molecules. The methods of the invention can be used in accordance with a wide range of fluid operations performed in plastic devices, including but not limited to reactions, incubations, dilutions, titrations, purifications, detections, mixing, binding assays, measuring assays (e.g., measurement of kinetics) and drug screening assays. Any number or combination of fluid operations may be performed according to the methods of the invention. More specifically, the successive fluid operations can comprise performing a genotyping process consisting of polymerase chain reaction (PCR), enzyme purification using shrimp alcaline phosphatase (SAP) and microsequencing (MIS). Particularly preferred first fluid operation is PCR.

Methods of the invention can be used to perform fluid operations in a wide variety of plastic devices. Such devices include but are not limited to tests tubes, multi-well plates, microtiter plates, pipette tips, reaction wells and microcentrifuge tubes. Such devices can be made of, e.g., polydimethylsiloxanes, polymethylmethacrylate, polyurethane, polyvinylchloride, polystyrene, polysulfone, polycarbonate, polytetrafluoroethylene, polypropylene, polyethylene, polymethylpenten, polyethylene, fluoropolymers and elastomers. In a preferred embodiment, the method of the present invention is directed to perform fluid operations in microtiter plates, which are commonly used in a variety of biological procedures. In general, one biological reaction is carried out in one well of one microtiter plate. However, some processes require successive reactions and it is thus efficient and beneficial to decrease adsorption of organic materials onto the surface of microtiter plate wells in order to perform two or more successive reactions in the same well of one unique microtiter plate. In particularly preferred embodiments, the methods of the present invention are directed to successive fluid operations performed in high-density microtiter plate, e.g., microtiter plates of 96, 384, 1536, or more wells.

Preferred polymers for use in performing fluid operations in plastic devices are from a family of homopolymers, including but not limited to polyacrylamides, such as polyacrylamide (PAM), N-isopropylacrylamide (NIPAM) and polydimethylacrylamide (PDMA), propylene glycol (PG), ethylene glycol (EG), polyglycols including polypropylene glycols (PPG) and polyethylene glycols (PEG), propylene oxide (PO) and ethylene oxide (EO), and polyoxides including polypropylene oxides (PPO) and polyethylene oxides (PEO), polydimethylsiloxane (PDMS), and polyvinylpyrolidone. In most preferred embodiments, block copolymers are used, including for example block copolymers of the polymers listed herein are used, including for example block copolymers of PPG and PEG and PAM and NIPAM and PDMS, and further including block copolymers such as polyacrylamide-block-N-isopropylacrylamide (PAM-NIPAM) and polydimethylsiloxane-block-polyethyleneglycol (PDMS-PEG).

The invention also relates to kits for performing fluid operations in plastic devices using the methods of the present invention. Such kits comprise (a) an aqueous composition comprising a polymer as described herein; (b) reagents for performing the fluid operations; and (c) a notice recommending the quantity of said composition that should be added to the reagents. Alternatively, the polymer may be comprised in the reagents. The kit may be directed to perform a single fluid operation or a process comprising several fluid operations. The composition comprising said polymer may be added to all reagents or to at least one reagent for performing any of the fluid operations. In particularly preferred embodiments, the kit using the method of the present invention is a kit for performing PCR, or for performing a process comprising a PCR reaction. Even more preferably, the kit using the methods of the present invention is a kit for performing genotyping processes.

While the preferred embodiment of the invention has been illustrated and described, it will be appreciated that various changes can be made therein by the one skilled in the art without departing from the spirit and scope of the invention.

EXAMPLES

Example 1

Preparation of a Surface Adsorbing Polymer

A preferred polymer, PDMA, was synthesized according to the following protocol. 2.8 g of N,N-dimethylacrylamide was dissolved in 30 ml of a MiliQ water and degassed for 2 hours with nitrogen. Subsequently, a redox couple consisting of sodium metabisulfite ($Na_2S_2O_5$, 0.451 ml, concentration of 2.5 g/l) ammonium persulfate ($Na_2S_2O_8$, 0.451 ml, concentration of 20 g/l) was added to the acrylamide solution. The solution was left to polymerize for 3 hours under permanent stirring. (Viovy, J.-L., Hourdet, D., Sudor, J., French Patent No. 98 16676; J.Sudor et al., Electrophoresis, 2001, 22:720–28). The polymerized polydimethylacrylamide (PDMA) was purified by ultrafiltration (Milipore, USA) with a membrane having a molecular weight cut off of 100 000 daltons. The purified PDMA was freeze-dried overnight.

Example 2

Conducting a Biological Reaction: PCR

Silicon microfluidic substrates having channels disposed therein were rinsed with hot water (~90° C.) prior to use. Each channel (with a volume of 10 µl) was rinsed with 1 ml of water by means of a 5 ml polypropylene syringe. The substrates were then dried by using the syringe to blow air through the channels.

A micropipette of 10 µl was used to fill the channels with PCR mix. The tip of the pipette cone was placed at the entrance of the channels and 10 µl mix was ejected into the channels.

Channels to be coated with PDMA received a PCR mix containing $MgCl_2$ (2 mM), nucleotides dATP, dGTP, dCTP, dTTP(200 µM each), forward and reverse primer (300 nM each), TaqGold (Perkin Elmer) (0.04 U/µl), DNA (1 ng/µl), PDMA (0.1%) and $H_2O$.

Channels to be coated with BSA received a PCR mix containing $MgCl_2$ (2 mM), nucleotides dATP, dGTP, dCTP, dTTP(200 µM each), forward and reverse primer (300 nM each), TaqGold (Perkin Elmer) (0.04 U/µl), DNA (1 ng/µl), BSA (0.5%) and $H_2O$.

An adhesive aluminum sheet was used to seal the channels to prevent evaporation during the thermocycling. The sheet was only put on the upper side of the chip. The backside of the chips was left "clean" to provide the best thermal transfer during the thermocycling.

Once sealed, the chip was put on a flat block on a Tetrade-thermocycler (MJ Research). A tiny drop of oil was put between the chip and the flat block to provide a better thermal contact and, as a consequence, a better heat transfer.

The chip with the PCR mix was, following preactivation of the Taq polymerase (94° C. for 10 min), cycled for 35 cycles of 30 s at 94° C., 60 s at 55° C. and 30 s at 72° C.

The mix was then recovered from the channels and the result was analysed with gel electrophoresis (agarose gel) and with quantification of double stranded DNA with the intercalating fluorescent dye PicoGreen.

Example 3

Microsequencing in a Microtiter Plate

The below protocol allows for a genotyping procedure to be performed in a 384-well microtiter plate without changing wells Microsequencing A PCR mix was prepared with Synperonic P105 block-copolymer (final concentration of 0.5%), 2 µl of DNA (1 ng/µl), 2 µl of TaqGold (0.02 U/µl) and 2 µl of PCR primers (300 nM). A purification mix was prepared with 4 µl of SAP (0.4U/µl) and 4 µl of EXO (0.2U/µl). A MIS mix was prepared with 8 µl of Thermosequenase (0.05U/µl), 8 µl of MIS oligonucleotides (0.5 µm) and 8 µl of labeled ddNTPS (9 nM).

2 µl of PCR mix was added to the well of the microtiter plate. The microtiter plate was, following preactivation of the Taq polymerase (94° C. for 10 mn), cycled for 35 cycles of 30 s at 94° C., 60 s at 55° C. and 30 s at 72° C. An elongation step was performed at the end of the cycling (72° C. for 7 mn). 2 µl of purification mix were added to same well, and the microtiter plate was incubated for 30 min at 37° C. and for 10 mn at 94° C. Finally, 4 µl of MIS mix were added to the same well, and the microtiter plate was incubated for 1 min at 94° C. and cycled for 20 cycles of 15 s at 55° C., 5 s at 72° C. and 10 s at 94° C.

Analysis of Genotyping Data

Figure 5:
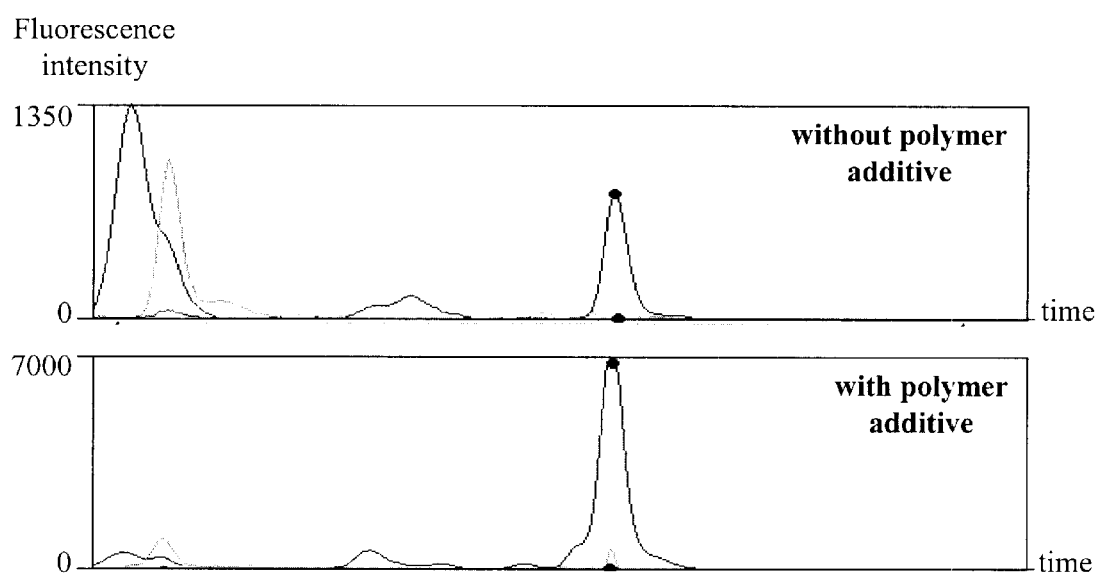
FIG. 5 shows the effect of copolymer addition on the intensity of the specific signal obtained after a genotyping process performed as described in Example 3.
Figure 6:
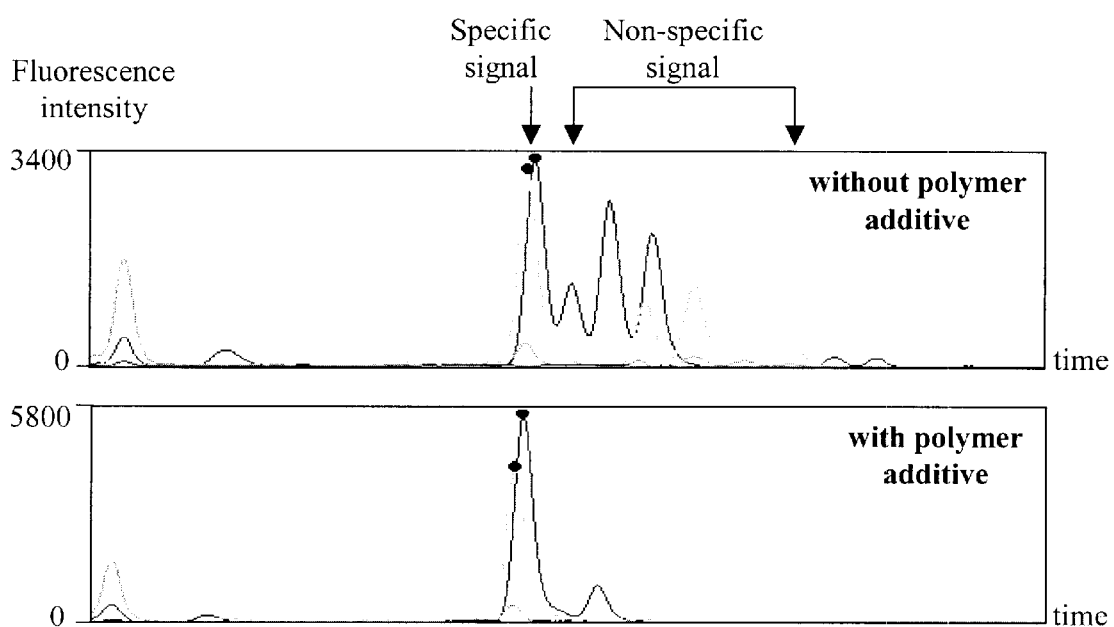
FIG. 6 shows the effect of copolymer addition on the specificity of the signal obtained after a genotyping process performed as described in Example 3.

Using Genset's proprietary software, the fluorescent signal from the microsequencing procedure is analyzed. However, one commonly encountered problem from the genotyping procedure is adsorption of deoxynucleotides (dNTPs) onto the surface of microtiter plates, particularly during genotyping processes. Adsorption of dNTPs added during the first step of a genotyping procedure (e.g., PCR) onto the surface of a microtiter plate render them less accessible to shrimp alkaline phosphatase (SAP) during subsequent steps (e.g., enzymatic purification), and the adsorbed dNTPs are not dephosphorylated. As dNTPs release from the surface of the microtiter plate at high temperature (e.g., during the denaturation of EXO and SAP enzymes or during the temperature cycling of the MIS reactions), they dramatically contaminate the third step of the genotyping process (i.e., MIS). As a result, the MIS oligonucleotide product may be extended by more than one base (dNTPs); thus the SNP specific fluorenscently-labeled ddNTPs may be incorrectly incorporated into the oligonucleotide product several bases downstream from the SNP site of interest creating non-specific signals (See FIGS. 5 and 6).

What is claimed is:

1. A method of decreasing adsorption of an organic material to a surface, comprising:
   a) providing a fluid sample comprising an organic material;
   b) adding an effective amount of a surface adsorbing polymer to said fluid sample;
   c) contacting said fluid sample comprising said organic material and said surface adsorbing polymer to a surface; and
   d) performing a fluid operation;
   wherein:
   1) said surface adsorbing polymer binds non-covalently to said surface;
   2) said surface adsorbing polymer reduces the amount of adsorption of said organic material to said surface;
   3) said surface adsorbing polymer is not one of the reactants of said fluid operation or is added in excess of the amount normally added to said fluid sample;
   4) said surface adsorbing polymer does not inhibit the fluid operation;
   5) said fluid operation is a chemical reaction, a dilution, a titration, a detection, a mixing and drug screening assay, or a biochemical reaction; and
   6) said surface is part of an apparatus and said surface is selected from the group consisting of ninety-six (96) well microtiter plates, three hundred eighty-four (384) well microtiter plates, one thousand five hundred thirty-six (1536) well microtiter plates, microtiter plates comprising more than one thousand five hundred thirty-six (1536) wells, microcentrifuge tubes, test tubes, pipettes, pipette tips, and multi-well plates.

2. The method according to claim 1, wherein said surface adsorbing polymer is selected from any one of: polyacrylamide, polydimethylacrylamide, N-isopropylacrylamide, ethylene glycol, propylene glycol, polyethylene glycols, polypropylene glycols, ethylene oxide, propylene oxide, polyethylene oxides and polypropylene oxides, or a block-copolymer comprising two or more polymers selected from the group consisting of polyacrylamide, polydimethylacrylamide, N-isopropylacrylamide, polyethylene glycols, polypropylene glycols, polyethylene oxides, polypropylene oxides and polydimethylsiloxane.

3. The method according to claim 1, wherein said surface comprises a polymer selected from the group consisting of polystyrene, polypropylene, polymethyl methacrylate, polyvinyl chloride, polymethyl penten, polyethylene, polycarbonate, polysulfone, polystyrene, fluoropolymers, polyamides, silicones and customers.

4. The method according to claim 1, wherein said:
   a) fluid sample is an aqueous solution;
   b) fluid sample is a non aqueous solution;
   c) fluid operation is a biochemical reaction selected from the group consisting of polymerase chain reactions (PCR) and primer extension reactions;
   d) organic material comprises deoxynucleotide triphosphates (dNTPs);
   e) surface adsorbing polymer has a molecular weight of at least $1 \times 10^6$ daltons
   f) organic material is nucleic acids, dNTPs, dideoxynucleotide triphosphates (ddNTPs), amino acids, proteins, lipids, or chemical compounds; or
   g) surface adsorbing polymer is not nucleic acids, dNTPs, ddNTPs, amino acids, proteins, lipids, or other biomolecules.

5. The method according to claim 4, wherein said fluid sample is an aqueous solution.

6. The method according to claim 4, wherein said fluid sample is a non-aqueous solution.

7. The method according to claim 4, wherein said fluid operation is a primer extension reaction.

8. The method according to claim 4, wherein said organic material comprises dNTPs.

9. The method according to claim 4, wherein said organic material is nucleic acids.

10. The method according to claim 4, wherein said organic material is ddNTPs.

11. The method according to claim 4, wherein said organic material is amino acids.

12. The method according to claim 4, wherein said organic material is proteins.

13. The method according to claim 4, wherein said organic material is lipids.

14. The method according to claim 4, wherein said organic material is chemical compounds.

15. The method according to claim 4, wherein said surface adsorbing polymer is not nucleic acids, dNTPs, ddNTPs, amino acids, proteins, lipids, or other biomolecules.

16. The method according to claim 4, wherein said surface adsorbing polymer has a molecular weight of at least $1 \times 10^6$ daltons.

17. The method according to claim 4, wherein said fluid operation is a polymerase chain reaction.

18. The method according to claim 1, wherein said fluid operation is a chemical reaction.

19. The method according to claim 1, wherein said fluid operation is a dilution.

20. The method according to claim 1, wherein said fluid operation is a titration.

21. The method according to claim 1, wherein said fluid operation is a detection.

22. The method according to claim 1, wherein said fluid operation is a mixing and drug screening assay.

23. The method according to claim 1, wherein said fluid operation is a biochemical reaction.

24. The method according to claim 23, wherein said biochemical reaction is a PCR reaction.

25. The method according to claim 23, wherein said biochemical reaction is a microsequencing (MIS) reaction.

26. The method according to claim 1, wherein said surface is a ninety-six (96) well microliter plate.

27. The method according to claim 1, wherein said surface is a three hundred eighty-four (384) well microtiter plates.

28. The method according to claim 1, wherein said surface is a one thousand five hundred thirty-six (1536) well microtiter plates.

29. The method according to claim 1, wherein said surface is a microtiter plate comprising more than one thousand five hundred thirty-six (1536) wells.

30. The method according to claim 1, wherein said surface is a microcentrifuge tube.

31. The method according to claim 1, wherein said surface is a test tube.

32. The method according to claim 1, wherein said surface is a pipette.

33. The method according to claim 1, wherein said surface is a pipette tip.

34. The method according to claim 1, wherein said surface is a microfluidic substrate comprising reaction wells.

35. The method according to claim 1, wherein said surface adsorbing polymer has a molecular weight of at least $1 \times 10^6$ daltons.

36. The method according to claim 1, wherein said surface adsorbing polymer has a molecular weight of at least $5 \times 10^4$ daltons.

37. A method of decreasing adsorption of an organic material to a surface, comprising:
   a) providing a fluid sample comprising an organic material;
   b) adding an effective amount of a surface adsorbing polymer to said fluid sample, wherein said surface adsorbing polymer has a molecular weight of at least $5 \times 10^{4^4}$ daltons;
   c) contacting said fluid sample comprising said organic material and said surface adsorbing polymer to a surface; and
   d) performing a fluid operation;
   wherein:
   1) said surface adsorbing polymer binds non-covalently to said surface;
   2) said surface adsorbing polymer reduces the amount of adsorption of said organic material to said surface;
   3) said surface adsorbing polymer is not one of the reactants of said fluid operation or is added in excess of the amount normally added to said fluid sample;
   4) said surface adsorbing polymer does not inhibit the fluid operation; and
   5) said surface is part of an apparatus and said surface is selected from the group consisting of microtiter plates, microcentrifuge tubes, microchannels, test tubes, pipettes, pipette tips, multi-well plates, and microfluidics substrates.

38. The method according to claim 37, wherein said surface adsorbing polymer has a molecular weight of at least $1 \times 10^6$ daltons.

39. The method according to claim 37, wherein said surface comprises a polymer selected from the group consisting of polystyrene, polypropylene, polymethyl methacrylate, polyvinyl chloride, polymethyl penten, polyethylene, polycarbonate, polysulfone, polystyrene, fluoropolymers, polyamides, silicones and elastomers, and further wherein said surface makes up an apparatus is selected from the group consisting of microliter plates, microcentrifuge tubes, channels, microchannels, test tubes, multi-well plates, and reactions wells.

40. The method according to claim 37, wherein said:
   a) fluid sample is an aqueous solution;
   b) fluid sample is a non aqueous solution;
   c) fluid operation is a polymerase chain reaction (PCR) or a primer extension reaction;
   d) organic material comprises deoxynucleotide triphosphates (dNTPs);
   e) surface adsorbing polymer has a molecular weight of at least $1 \times 10^6$ daltons;
   f) organic material is nucleic acids, dNTPs, dideoxynucleotide triphosphates (ddNTPs), amino acids, proteins, lipids, or chemical compounds; or
   g) surface adsorbing polymer is not nucleic acids, dNTPs, ddNTPs, amino acids, proteins, lipids, or other biomolecules.

41. The method according to claim 37, wherein said surface adsorbing polymer is selected from any one of: polyacrylamide, polydimethylacrylamide, N-isopropylacrylamide, ethylene glycol, propylene glycol, polyethylene glycols, polypropylene glycols, ethylene oxide, propylene oxide, polyethylene oxides and polypropylene oxides, or a block-copolymer comprising two or more polymers selected from the group consisting of polyacrylamide, polydimethylacrylamide, N-isopropylacrylamide, polyethylene glycols, polypropylene glycols, polyethylene oxides, polypropylene oxides and polydimethylsiloxane.

* * * * *

UNITED STATES PATENT AND TRADEMARK OFFICE
CERTIFICATE OF CORRECTION

PATENT NO. : 6,709,692 B2
DATED : March 23, 2004
INVENTOR(S) : Jan Sudor

It is certified that error appears in the above-identified patent and that said Letters Patent is hereby corrected as shown below:

Title page,
Item [54], Title, "SURFACE ABSORBING POLYMERS AND THE USES THEREOF TO TREAT HYDROPHOBIC OR HYDROPHILICS SURFACES" should read -- SURFACE ADSORBING POLYMERS AND THE USES THEREOF TO TREAT HYDROPHOBIC OR HYDROPHILIC SURFACES --.

Column 19,
Line 47, "(PDMSPEG)" should read -- (PDMS-PEG) --.

Column 20,
Line 21, "1 is the " should read -- $l$ is the --
Line 51, and 52, "than 1" should read -- than $l$ --

Column 28,
Line 8-9, "PCT/IB00/01 137" should read -- PCT/IB00/01137 --.

Column 34,
Line 13, "customers" should read -- elastomers --.

Column 35,
Line 8, "microliter" should read -- microtiter --.
Line 40, "$5 \times 104^4$" should read -- $5 \times 10^4$ --, Column 36,
Line 19, "microliter" should read -- microtiter --.

Signed and Sealed this

Twenty-fifth Day of May, 2004

JON W. DUDAS
*Acting Director of the United States Patent and Trademark Office*